United States Patent
Smith et al.

(10) Patent No.: US 11,596,313 B2
(45) Date of Patent: Mar. 7, 2023

(54) PHOTOACOUSTIC TARGETING WITH MICROPIPETTE ELECTRODES

(71) Applicants: Barbara Smith, Scottsdale, AZ (US); Christopher Miranda, Tempe, AZ (US)

(72) Inventors: Barbara Smith, Scottsdale, AZ (US); Christopher Miranda, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 449 days.

(21) Appl. No.: 16/159,167

(22) Filed: Oct. 12, 2018

(65) Prior Publication Data

US 2019/0110691 A1   Apr. 18, 2019

Related U.S. Application Data

(60) Provisional application No. 62/572,338, filed on Oct. 13, 2017.

(51) Int. Cl.
*A61B 5/00* (2006.01)
*G01N 29/24* (2006.01)
(Continued)

(52) U.S. Cl.
CPC .......... *A61B 5/0095* (2013.01); *A61B 5/0033* (2013.01); *A61B 5/0042* (2013.01);
(Continued)

(58) Field of Classification Search
CPC ... A61B 5/0033; A61B 5/0042; A61B 5/0059; A61B 5/0095; A61B 5/065;
(Continued)

(56) References Cited

U.S. PATENT DOCUMENTS

| | | |
|---|---|---|
| 4,267,732 A | 5/1981 | Quate |
| 5,752,518 A | 5/1998 | Mcgee et al. |

(Continued)

FOREIGN PATENT DOCUMENTS

| | | | |
|---|---|---|---|
| CN | 2061692 U | * | 9/1990 |
| FR | 2997502 A1 | | 5/2014 |

(Continued)

OTHER PUBLICATIONS

Espacenet translation of CN 2061692 (generated Mar. 17, 2021) (Year: 1990).*

(Continued)

*Primary Examiner* — Joseph M Santos Rodriguez
*Assistant Examiner* — Maria Christina Talty
(74) *Attorney, Agent, or Firm* — Michael Best & Friedrich LLP

(57) ABSTRACT

Photoacoustic targeting systems for intracellular recording. In one embodiment, the photoacoustic targeting system includes a light source, a micropipette electrode, an acoustic transducer, and a controller. The light source is configured to emit pulsed light. The micropipette electrode is configured to deliver the pulsed light to a target cell. The acoustic transducer is configured to receive photoacoustic signals generated due to optical absorption of light energy by the target cell. The controller is configured to determine a position of the micropipette electrode relative to the target cell based on the photoacoustic signals.

14 Claims, 12 Drawing Sheets

(51) Int. Cl.
*A61B 5/06* (2006.01)
*G01N 21/17* (2006.01)

(52) U.S. Cl.
CPC ............ *A61B 5/0059* (2013.01); *A61B 5/065* (2013.01); *G01N 21/1702* (2013.01); *G01N 29/2418* (2013.01); *G01N 2291/02466* (2013.01)

(58) Field of Classification Search
CPC .............. A61B 5/0093; G01N 21/1702; G01N 2291/02466; G01N 29/2418
See application file for complete search history.

(56) References Cited

U.S. PATENT DOCUMENTS

| | | | |
|---|---|---|---|
| 8,932,223 | B2 | 1/2015 | Emelianov et al. |
| 9,618,445 | B2 | 4/2017 | Sun et al. |
| 10,107,613 | B2 | 10/2018 | Jiao et al. |
| 10,795,440 | B1* | 10/2020 | Chevillet ............ A61B 5/0042 |
| 2007/0299341 | A1* | 12/2007 | Wang ................... A61B 5/0093 600/443 |
| 2010/0079580 | A1 | 4/2010 | Waring, IV |
| 2010/0245766 | A1 | 9/2010 | Zhang et al. |
| 2011/0098530 | A1 | 4/2011 | Yamane |
| 2011/0282192 | A1 | 11/2011 | Axelrod et al. |
| 2011/0301458 | A1* | 12/2011 | Li ........................ A61B 8/4477 600/437 |
| 2012/0275262 | A1 | 11/2012 | Song et al. |
| 2013/0158383 | A1 | 6/2013 | Cheng et al. |
| 2013/0216114 | A1 | 8/2013 | Courtney et al. |
| 2014/0066743 | A1 | 3/2014 | Nakajima et al. |
| 2014/0142404 | A1 | 5/2014 | Wang et al. |
| 2015/0160168 | A1* | 6/2015 | Irisawa ................... F21V 13/02 73/645 |
| 2015/0226845 | A1 | 8/2015 | Witte et al. |
| 2015/0247999 | A1 | 9/2015 | Ntziachristos et al. |
| 2015/0327768 | A1* | 11/2015 | Oyama ................... A61B 5/748 600/407 |
| 2016/0003777 | A1 | 1/2016 | Schmitt-Manderbach et al. |
| 2016/0143542 | A1 | 5/2016 | Bossy et al. |
| 2016/0242651 | A1* | 8/2016 | Wang ................... A61B 8/0808 |
| 2016/0249812 | A1* | 9/2016 | Wang .................. A61B 5/14542 600/407 |
| 2016/0250073 | A1 | 9/2016 | Gooding et al. |
| 2016/0305914 | A1 | 10/2016 | Wang et al. |
| 2016/0356746 | A1 | 12/2016 | Piestun et al. |
| 2017/0055841 | A1 | 3/2017 | Mueller et al. |
| 2017/0065182 | A1 | 3/2017 | Wang et al. |
| 2017/0105626 | A1* | 4/2017 | Irisawa ................ A61B 5/0035 |
| 2017/0156600 | A1 | 6/2017 | Ntziachristos et al. |
| 2017/0367682 | A1 | 12/2017 | Smith et al. |
| 2018/0055343 | A1 | 3/2018 | Yang et al. |
| 2018/0078143 | A1 | 3/2018 | Pramanik et al. |
| 2018/0132728 | A1 | 5/2018 | Wang et al. |
| 2018/0214119 | A1 | 8/2018 | Mehrmohammadi et al. |
| 2018/0235570 | A1 | 8/2018 | Fukushima |
| 2019/0046159 | A1 | 2/2019 | Smith et al. |
| 2019/0175938 | A1 | 6/2019 | Rezaie et al. |
| 2019/0227038 | A1 | 7/2019 | Wang et al. |
| 2019/0282069 | A1 | 9/2019 | Smith et al. |
| 2020/0056986 | A1 | 2/2020 | Wang et al. |
| 2020/0160522 | A1 | 5/2020 | Merlo et al. |
| 2020/0173965 | A1 | 6/2020 | Sangu |
| 2020/0340954 | A1 | 10/2020 | Smith et al. |
| 2020/0398268 | A1 | 12/2020 | Smith et al. |
| 2021/0080708 | A1 | 3/2021 | Sangu |
| 2022/0151496 | A1 | 5/2022 | Waldner et al. |

FOREIGN PATENT DOCUMENTS

| | | | |
|---|---|---|---|
| IN | 308501 | B | 4/2019 |
| WO | 2008075299 | A1 | 6/2008 |
| WO | 2008100386 | A2 | 8/2008 |
| WO | 2009050632 | A1 | 4/2009 |
| WO | 2015175431 | A1 | 11/2015 |
| WO | 2015183092 | A1 | 12/2015 |

OTHER PUBLICATIONS

Jonathan Knight and Fei Yu, Apr. 2019, Photonics Spectra, Features, pp. 1-7 (Year: 2019).*
Jiayi Zhang et al., "Integrated device for optical stimulation and spatiotemporal electrical recording of neural activity in light-sensitized brain tissue," Apr. 6, 2009, Journal of Neural Engineering, 6, pp. 1-13 (Year: 2009).*
Nily Kuck et al., "Visible electroluminescent subwavelength point source of light,"Apr. 27, 1992, Applied Physics Letters, 61, 2, pp. 139-141 (Year: 1992).*
Thor Labs "Achromatic Pairs" 2011 (Year: 2011).*
Abbas, J. J.; Smith, B.; Poluta, M.; Velazquez-Berumen, A., Improving health-care delivery in lowresource settings with nanotechnology:Challenges in multiple dimensions. Nanobiomedicine 2017, 4, 1849543517701158.
Abe, Y.-W. Shi, Y. Matsuura, and M. Miyagi, "Flexible small-bore hollow fibers with an inner polymer coating," Opt. letters 25, 150-152 (2000).
Addington, CP, Dharmaraj, S, Heffernan, JM, Sirianni, RW, Stabenfeldt, SE. Hyaluronic acid-laminin hydrogels increase neural stem cell transplant retention and migratory response to SDF-1α. Matrix Biology. 2016;16:30210-4. DOI: 10.1016/j.matbio.2016.09.007.
Anand, S.; Kumar, S. S.; Muthuswamy, J., Autonomous control for mechanically stable navigation of microscale implants in brain tissue to record neural activity. Biomedical Microdevices 2016, 18 (4).
Anderson, T. R.; Hu, B.; Iremonger, K.; Kiss, Z. H. T., Selective attenuation of afferent synaptic transmission as a mechanism of thalamic deep brain stimulation-induced tremor arrest. Journal of Neuroscience 2006, 26 (3), 841-850.
Anderson, T. R.; Huguenard, J. R.; Prince, D. A., Differential effects of Na plus-K plus ATPase blockade on cortical layer V neurons. Journal of Physiology—London 2010, 588 (22), 4401-4414.
Andrasfalvy, B. K.; Galinanes, G. L.; Huber, D.; Barbie, M.; Macklin, J. J.; Susumu, K.; Delehanty, J. B.; Huston, A. L.; Makara, J. K.; Medintz, I. L., Quantum dot-based multiphoton fluorescent pipettes for targeted neuronal electrophysiology. Nat. Methods 2014, 11 (12), 1237-1241.
Annecchino, A. R. Morris, C. S. Copeland, O. E. Agabi, P. Chadderton, and S. R. Schultz, "Robotic automation of in vivo two-photon targeted whole-cell patch-clamp electrophysiology," Neuron 95, 1048-1055 (2017).
Aravanis, A. M.; Wang, L. P.; Zhang, F.; Meltzer, L. A.; Mogri, M. Z.; Schneider, M. B.; Deisseroth, K., An optical neural interface: in vivo control of rodent motor cortex with integrated fiberoptic and optogenetic technology. Journal of Neural Engineering 2007, 4 (3), S143-S156.
Aston-Jones, G.; Deisseroth, K., Recent advances in optogenetics and pharmacogenetics. Brain Research 2013, 1511, 1-5.
Badu-Tawiah, A. K.; Lathwal, S.; Kaastrup, K.; Al-Sayah, M.; Christodouleas, D. C.; Smith, B. S.; Whitesides, G. M.; Sikes, H. D., Polymerization-based signal amplification for paper-based immunoassays. Lab on a chip 2015, 15 (3), 355-659.
Balaic, D. X.; Nugent, K. A., x-ray optics of tapered capillaries. Applied Optics 1995, 34 (31), 7263-7272.
Beard, P., Biomedical photoacoustic imaging. Interface Focus 2011, 1 (4), 602-631.
Beaulieu-Laroche, L.; Harnett, M. T., Dendritic Spines Prevent Synaptic Voltage Clamp. Neuron 2018, 97 (1), 75-82.
Bilderback, D. H.; Fontes, E., Glass capillary optics for making x-ray beams of 0.1 to 50 microns diameter. AIP Conference Proceedings 1997, Medium: X; Size: pp. 147-155.
Billet, A.; Froux, L.; Hanrahan, J. W.; Becq, F., Development of Automated Patch Clamp Technique to Investigate CFTR Chloride Channel Function. Frontiers in Pharmacology 2017, 8.

(56) References Cited

OTHER PUBLICATIONS

Bohndiek, S. Bodapati, D. Van De Sompel, S.-R. Kothapalli, and S. S. Gambhir, "Development and application of stable phantoms for the evaluation of photoacoustic imaging instruments," PloS one 8, e75533 (2013).
Bornstein, J. C.; Furness, J. B., correlated electrophysiological and histochemical-studies of submucous neurons and their contribution to understanding enteric neural circuits. Journal of the Autonomic Nervous System 1988, 25 (1), 1-13.
Boyden, E. S.; Zhang, F.; Bamberg, E.; Nagel, G.; Deisseroth, K., Millisecond-timescale, genetically targeted optical control of neural activity. Nature Neuroscience 2005, 8 (9), 1263-1268.
Chen, C. C.; Cang, C. L.; Fenske, S.; Butz, E.; Chao, Y. K.; Biel, M.; Ren, D. J.; Wahl-Schott, C.; Grimm, C., Patch-clamp technique to characterize ion channels in enlarged individual endolysosomes. Nat. Protoc. 2017, 12 (8), 1639-1658.
Dox, B.; Laufer, J. G.; Arridge, S. R.; Beard, P. C., Quantitative spectroscopic photoacoustic imaging: a review. J. Biomed. Opt. 2012, 17(6).
Sullen, D. K.; Stabenfeldt, S. E.; Simon, C. M.; Tate, C. C.; LaPlaca, M. C., In vitro neural injury model for optimization of tissue-engineered constructs Journal of Neuroscience Research 2007, 85 (16), 3642-3651.
De La Zerda, Adam, et al. "Carbon nanotubes as photoacoustic molecular imaging agents in living mice." Nature nanotechnology 3.9 (2008): 557.
Deisseroth, K., Optogenetics. Nat. Methods 2011, 8 (1), 26-29.
Desai, N. S.; Siegel, J. J.; Taylor, W.; Chitwood, R. A.; Johnston, D., MATLAB-based automated patch-clamp system for awake behaving mice. Journal of Neurophysiology 2015, 114 (2), 1331-1345.
Dika et al., Early experiences and integration in the persistence of first-generation college students in STEM and non-STEM majors Journal of Research in Science Teaching 2016, 53 (3), 368-383.
Dunn, R. C., Near-field scanning optical microscopy. Chemical reviews 1999, 99 (10), 2891-2928.
Fan, B.; Li, W., Miniaturized optogenetic neural implants: a review. Lab on a Chip 2015, 15 (19), 3838-3855.
Fenno, L.; Yizhar, O.; Deisseroth, K., The Development and Application of Optogenetics. In Annual Review of Neuroscience, vol. 34, Hyman, S. E.; Jessell, T. M.; Shatz, C. J.; Stevens, C. F.; Zoghbi, H. Y., Eds. 2011; vol. 34, pp. 389-412.
Frow, E. K.; Smith, B. S.; Ankeny, C. J. In Freshman design course: Device design for low-resource settings, ASEE Annual Conference and Exposition, Conference Proceedings, 2017.
Galanzha, E. I.; Shashkov, E. V.; Spring, P. M.; Suen, J. Y.; Zharov, V. P., In vivo, Noninvasive, Label-Free Detection and Eradication of Circulating Metastatic Melanoma Cells Using Two-Color Photoacoustic Flow Cytometry with a Diode Laser. Cancer Research 2009, 69 (20), 7926-7934.
Goddeyne, C.; Nichols, J.; Wu, C.; Anderson, T., Repetitive mild traumatic brain injury induces ventriculomegaly and cortical thinning in juvenile rats. Journal of Neurophysiology 2015, 113 (9), 3268-3280.
Gooch, C. L.; Pracht, E.; Borenstein, A. R., The burden of neurological disease in the United States: A summary report and call to action. Annals of neurology 2017, 81 (4), 479-484.
Grewe, B. F.; Langer, D.; Kasper, H.; Kampa, B. M.; Helmchen, F., High-speed in vivo calcium imaging reveals neuronal network activity with near-millisecond precision (vol. 7, p. 399, 2010) Nat Methods 2010, 7 (6), 479-479.
Hamill, O. P.; Marty, A.; Neher, E.; Sakmann, B.; Sigworth, F. J., improved patch-clamp techniques for high-resolution current recording from cells and cell-free membrane patches. Pflugers Arch. 1981, 391 (2), 85-100.
Harvey, C. D.; Collman, F.; Dombeck, D. A.; Tank, D. W., Intracellular dynamics of hippocampal place cells during virtual navigation. Nature 2009, 461 (7266), 941-U196.
Hayar, C. Gu, and E. D. Al-Chaer, "An improved method for patch clamp recording and calcium imaging of neurons in the intact dorsal root ganglion in rats," J. neuroscience methods 173, 74-82 (2008).

Hecht, B.; Sick, B.; Wild, U. P.; Deckert, V.; Zenobi, R.; Martin, O. J. F.; Pohl, D. W., Scanning near-field optical microscopy with aperture probes: Fundamentals and applications. Journal of Chemical Physics 2000, 112 (18), 7761-7774.
Helmchen, F.; Denk, W., Deep tissue two-photon microscopy. Nat. Methods 2005, 2 (12), 932-940.
Hu, S.; Maslov, K.; Wang, L. V., Second-generation optical-resolution photoacoustic microscopy with improved sensitivity and speed. Opt. Lett. 2011, 36 (7), 1134-1136.
Hurtado, S.; Newman, C. B.; Tran, M. C.; Chang, M. J., Improving the Rate of Success for Underrepresented Racial Minorities in STEM Fields: Insights from a National Project. New Directions for Institutional Research 2010, 148, 5-15.
Ishitani, T. T., Studying attrition and degree completion behavior among first-generation college students in the United States. The Journal of Higher Education 2006, 77 (5), 861-885.
Jansen, M. Wu, A. F. van der Steen, and G. van Soest, "Lipid detection in atherosclerotic human coronaries by spectroscopic intravascular photoacoustic imaging," Opt express 21, 21472-21484 (2013).
Karpiouk, B. Wang, J. Amirian, R. W. Smalling, and S. Y. Emelianov, "Feasibility of in vivo intravascular photoacoustic imaging using integrated ultrasound and photoacoustic imaging catheter," J. biomedical optics 17, 0960081-0960086 (2012).
Keene, A. C.; Waddell, S., *Drosophila* olfactory memory: single genes to complex neural circuits. Nature Reviews Neuroscience 2007, 8 (5), 341-354.
Khraiche, W Phillips*, N Jackson*, J Muthuswamy, "Sustained Elevation of Activity of Developing Neurons Grown on Polyamide Microelectrode Arrays (MEA) in Response to Ultrasound Exposure," Microsystem Technologies, doi:10.1007/s00542-016-3150-6, 2016.
Kim, E. Chung, H. Yamashita, K. E. Hung, A. Mizoguchi, R. Kucherlapati, D. Fukumura, R. K. Jain, and S. H. Yun, "In Vivo wide-area cellular imaging by side-view endomicroscopy," Nat. methods 7, 303 (2010).
Kim, Taeho et al. "Photoacoustic Imaging of Human Mesenchymal Stem Cells Labeled with Prussian Blue-Poly(l-lysine) Nanocomplexes." ACS nano vol. 11,9 (2017): 9022-9032. doi:10.1021/acsnano.7b03519.
Kitamura, B. Judkewitz, M. Kano, W. Denk, and M. Hausser, "Targeted patch-clamp recordings and single-cell electroporation of unla-beled neurons in vivo," Nat methods 5, 61-67 (2008).
Kodandaramaiah, G. L. Holst, I. R. Wickersham, A. C. Singer, G. T. Franzesi, M. L. McKinnon, C. R. Forest, and E. S. Boyden, "Assembly and operation of the autopatcher for automated intracellular neural recording in vivo," Nat. protocols 11, 634-654 (2016).
Vasilyev, D.; Merrill, T.; Iwanow, A.; Dunlop, J.; Bowlby, M., A novel method for patch-clamp automation. Pflugers Arch. 2006, 452 (2), 240-247.
Veerman, J. A.; Otter, A. M.; Kuipers, L.; van Hulst, N. F., High definition aperture probes for nearfield optical microscopy fabricated by focused ion beam milling. Applied Physics Letters 1998, 72 (24), 3115-3117.
Wang and S. Hu, "Photoacoustic tomography: in vivo imaging from organelles to organs," Science 335, 1458-1462 (2012).
Wang, A. Karpiouk, D. Yeager, J. Amirian, S. Litovsky, R. Smalling, and S. Emelianov, "Intravascular photoacoustic maging of lipid in atherosclerotic plaques in the presence of luminal blood," Opt. letters 37, 1244-1246 (2012).
Wang, C.-C.; Hennek, J. W.; Ainla, A.; Kumar, A. A.; Lan, W.-J.; Im, J.; Smith, B. S.; Zhao, M.; Whitesides, G. M., A Paper-Based "Pop-up" Electrochemical Device for Analysis of Beta-Hydroxybutyrate. Analytical Chemistry 2016, 88(12), 6326-6333.
Wang, J. L. Su, A. B. Karpiouk, K. V. Sokolov, R. W. Smalling, and S. Y. Emelianov, "Intravascular photoacoustic imaging," IEEE J. selected topics Quantum Electron. 16, 588-599 (2010).
Wang, L. V., Multiscale photoacoustic microscopy and computed tomography. Nature Photonics 2009, 3 (9), 503-509.
Wang, T. Ma, M. N. Slipchenko, S. Liang, J. Hui, K. K. Shung, S. Roy, M. Sturek, Q. Zhou, Z. Chen, and J.-X. Cheng, "High-speed

(56) References Cited

OTHER PUBLICATIONS intravascular photoacoustic imaging of lipid-laden atherosclerotic plaque enabled by a 2-khz barium nitrite raman laser," Sci. reports 4, 6889 (2014).
Wang, X. D.; Pang, Y. J.; Ku, G.; Xie, X. Y.; Stoica, G.; Wang, L. H. V., Noninvasive laser-induced photoacoustic tomography for structural and functional in vivo imaging of the brain. Nat. Biotechnol 2003, 21 (7), 803-806.
Wang, X. D.; Xie, X. Y.; Ku, G. N.; Wang, L. H. V., Noninvasive imaging of hemoglobin concentration and oxygenation in the rat brain using high-resolution photoacoustic tomography. J. Biomed Opt. 2006, 11 (2).
Weber, Judith, Paul C. Beard, and Sarah E. Bohndiek. "Contrast agents for molecular photoacoustic imaging." Nature methods 13.8 (2016): 639.
Wong, Terence TW, et al. "Fast label-free multilayered histology-like imaging of human breast cancer by photoacoustic microscopy." Science advances 3.5 (2017): e1602168.
Wu, I. Kolb, B. M. Callahan, Z. Su, W. Stoy, S. B. Kodandaramaiah, R. Neve, H. Zeng, E. S. Boyden, C. R. Forest, and A. A. Chubykin, "Integration of autopatching with automated pipette and cell detection in vitro," J. neurophysiology 116, 1564-1578 (2016).
Xu, Minghua, and Lihong V. Wang. "Photoacoustic imaging in biomedicine." Review of scientific instruments 77.4 (2006): 041101.
Yajuan, X.; Xin, L.; Zhiyuan, L., A comparison of the performance and application differences between manual and automated patch-clamp techniques Curr Chem Genomics 2012, 6, 87-92.
Yang, C. Favazza, J. Yao, R. Chen, Q. Zhou, K. K. Shung, and L. V. Wang, "Three-dimensional photoacoustic endoscopic imaging of the rabbit esophagus," PloS one 10, e0120269 (2015).
Yang, C. Favazza, R. Chen, J. Yao, X. Cai, K. Maslov, Q. Zhou, K. K. Shung, and L. V. Wang, "Simultaneous functional photoacoustic and ultrasonic endoscopy of internal organs in vivo," Nat. medicine 18, 1297-1302 (2012).
Yang, C. Favazza, R. Chen, K. Maslov, X. Cai, Q. Zhou, K. K. Shung, and L. V. Wang, "Volumetric photoacoustic endoscopy of upper gastrointestinal tract: ultrasonic transducer technology development," in Proc. SPIE, , vol. 7899 (2011), pp. 78990D1-78990D6.
Yang, K. Maslov, H.-C. Yang, Q. Zhou, K. K. Shung, and L. V. Wang, "Photoacoustic endoscopy," Opt. letters 34, 1591-1593 (2009).
Yang, R.; Lai, K. W. C.; Xi, N.; Yang, J., Development of automated patch clamp system for electrophysiology. In 2013 IEEE International Conference on Robotics and Biomimetics, ROBIO 2013, 2013; p. 2185.
Yang, R.; Tam, C. H.; Cheung, K. L.; Wong, K. C.; Xi, N.; Yang, J.; Lai, W. C. K., Cell Segmentation and Pipette Identification for Automated Patch Clamp Recording. Robotics and Biomimetrics 2014, 1 (20), 1-12.
Yao, K. Maslov, K. K. Shung, Q. Zhou, and L. V. Wang, "In vivo label-free photoacoustic microscopy of cell nuclei by excitation of dna and ma," Opt. letters 35,4139-4141 (2010).
Yizhar, O.; Fenno, L. E.; Davidson, T. J.; Mogri, M.; Deisseroth, K., Optogenetics in Neural Systems. Neuron 2011, 71(1), 9-34.
Zhang and P. C. Beard, "A miniature all-optical photoacoustic imaging probe," in Proc. SPIE, , vol. 7899 (2011), p. 78991F.
Zhang, C.; Maslov, K.; Wang, L. H. V., Subwavelength-resolution label-free photoacoustic microscopy of optical absorption in vivo. Opt. Lett. 2010, 35 (19), 3195-3197.
Zhang, H. F.; Maslov, K.; Stoica, G.; Wang, L. H. V., Functional photoacoustic microscopy for high-resolution and noninvasive in vivo imaging. Nat. Biotechnol. 2006, 24 (7), 848-851.
Zhang, J. Y.; Laiwalla, F.; Kim, J. A.; Urabe, H.; Van Wagenen, R.; Song, Y. K.; Connors, B. W.; Zhang, F.; Deisseroth, K.; Nurmikko, A. V., Integrated device for optical stimulation and spatiotemporal electrical recording of neural activity in light-sensitized brain tissue. Journal of Neural Engineering 2009, 6 (5).
Zharov, V. P.; Galanzha, E. I.; Shashkov, E. V.; Khlebtsov, N. G.; Tuchin, V. V., In vivo photoacoustic flow cytometry for monitoring of circulating single cancer cells and contrast agents. Opt. Lett. 2006, 31 (24), 3623-3625.
Zharov, V. P.; Galanzha, E. I.; Shashkov, E. V.; Kim, J. W.; Khlebtsov, N. G.; Tuchin, V. V., Photoacoustic flow cytometry: principle and application for real-time detection of circulating single nanoparticles, pathogens, and contrast dyes in vivo. J. Biomed. Opt. 2007, 12 (5).
Zhou, K. H. Lam, H. Zheng, W. Qiu, and K. K. Shung, "Piezoelectric single crystal ultrasonic transducers for biomedica applications," Prog, materials science 66, 87-111 (2014).
Zorzos, A. N.; Boyden, E. S.; Fonstad, C. G., Multiwaveguide implantable probe for light delivery to sets of distributed brain targets. Opt. Lett. 2010, 35 (24), 4133-4135.
Kodandaramaiah, S. B.; Boyden, E. S.; Forest, C. R.; New York Acad, S., In vivo robotics: the automation of neuroscience and other intact-system biological fields. In Conference Reports: Evolutionary Dynamics and Information Hierarchies in Biological Systems: Aspen Center for Physics Workshop and Cracking the Neural Code: Third Annual Aspen Brain Forums, Blackwell Science Publ: Oxford, 2013; vol. 1305, pp. 63-71.
Kodandaramaiah, S. B.; Franzesi, G. T.; Chow, B. Y.; Boyden, E. S.; Forest, C. R., Automated whole-cell patch-clamp electrophysiology of neurons in vivo. Nat. Methods 2012, 9 (6), 585-+.
Kodandaramaiah, S. B.; Holst, G. L.; Wickersham, I. R.; Singer, A. C.; Franzesi, G. T.; McKinnon, M. L.; Forest, C. R.; Boyden, E. S., Assembly and operation of the autopatcher for automated intracellular neural recording in vivo. Nat. Protoc. 2016, 11 (4), 634-654.
Kodandaramaish, S. B.; Flores, F. J.; Holst, G. L.; Singer, A. C.; Han, X.; Brown, E. N.; Boyden, E. S.; Forest, C. R., Multi-neuron intracellular recording in vivo via interacting autopatching robots. eLife 2018, 7, 19.
Kozodoy, A. T. Pagkalinawan, and J. A. Harrington, "Small-bore hollow waveguides for delivery of 3-mm laser radiation," Appl. optics 35, 1077-1082 (1996).
Ku, G.; Wang, X. D.; Xie, X. Y.; Stoica, G.; Wang, L. H. V., Imaging of tumor angiogenesis in rat brains in vivo by photoacoustic tomography. Applied Optics 2005, 44 (5), 770 775.
Kumar et al., From the Bench to the Field in Low-Cost Diagnostics: Two Case Studies. Angewandte Chemie International Edition 2015, 54 (20), 5836-5853.
LeChasseur, Y.; Dufour, S.; Lavertu, G.; Bories, C.; Deschenes, M.; Vallee, R.; De Koninck, Y., A microprobe for parallel optical and electrical recordings from single neurons in vivo. Nat Methods 2011, 8 (4), 319-U63.
Llinas, R. R., Intrinsic electrical properties of mammalian neurons and CNS function: a historical perspective. Frontiers in Cellular Neuroscience 2014, 8.
Long, L. Li, U. Knoblich, H. Zeng, and H. Peng, "3d image-guided automatic pipette positioning for single cell experiments in vivo," Sci. reports 5, 18426 (2015).
Long, M. A.; Jin, D. Z. Z.; Fee, M. S., Support for a synaptic chain model of neuronal sequence generation. Nature 2010, 468 (7322), 394-399.
Lu, W.; Huang, Q.; Geng, K. B.; Wen, X. X.; Zhou, M.; Guzatov, D.; Brecht, P.; Su, R.; Oraevsky, A.; Wang, L. V.; Li, C., Photoacoustic imaging of living mouse brain vasculature using hollow gold nanospheres. Biomaterials 2010, 31 (9), 2617-2626.
Lusk, Joel F., et al. "Photoacoustic Flow System for the Detection of Ovarian Circulating Tumor Cells Utilizing Copper Sulfide Nanoparticles." ACS Biomaterials Science & Engineering (2019).
Mallidi, S.; Luke, G. P.; Emelianov, S., Photoacoustic imaging in cancer detection, diagnosis, and treatment guidance. Trends in Biotechnology 2011, 29 (5), 213-221.
Margrie, A. H. Meyer, A. Caputi, H. Monyer, M. T. Hasan, A. T. Schaefer, W. Denk, and M. Brecht, "Targeted whole-cell recordings in the mammalian brain in vivo," Neuron 39, 911-918 (2003).
Markram, H.; Lubke, J.; Frotscher, M.; Roth, A.; Sakmann, B., Physiology and anatomy of synaptic connections between thick tufted pyramidal neurones in the developing rat neocortex. Journal of Physiology-London 1997, 500 (2), 409-440.
Maslov, K.; Zhang, H. F.; Hu, S.; Wang, L. V., Optical-resolution photoacoustic microscopy for in vivo imaging of single capillaries. Opt. Lett. 2008, 33 (9), 929-931.

(56) References Cited

OTHER PUBLICATIONS

Matsuura, T. Abel, and J. A. Harrington, "Optical properties of smallbore hollow glass waveguides," Appl. optics 34, 3842-6847 (1995).

Matsuura, T. Abel, J. Hirsch, and J. Harrington, "Small-bore hollow waveguide for delivery of near singlemode ir laser radiation," Electron. Lett. 30, 1688-1690 (1994).

Miranda et al., "Side-viewing Photoacoustic Capillary Endoscope," 2018, Optics Letters, 1-4.

Miranda, C.; Barkley, J.; Smith, B. S., Intrauterine photoacoustic and ultrasound imaging probe. J. Biomed. Opt. 2018, 23 (4), 9.

Miranda, Christopher, et al. "Photoacoustic micropipette." Applied Physics Letters 113.26 (2018): 264103.

Neher, E.; Sakmann, B., single-channel currents recorded from membrane of denervated frog muscle-fibers. Nature 1976, 260 (5554), 799-802.

Nichols, J.; Bjorklund, G. R.; Newbern, J.; Anderson, T., Parvalbumin fast-spiking interneurons are selectively altered by paediatric traumatic brain injury. Journal of Physiology—London 2018, 596(7), 1277-1293.

Nichols, J.; Perez, R.; Wu, C.; Adelson, P. D.; Anderson, T., Traumatic Brain Injury Induces Rapid Enhancement of Cortical Excitability in Juvenile Rats. Cns Neuroscience & Therapeutics 2015, 21 (2), 193-203.

Olsen, S. R.; Wilson, R. I., Cracking neural circuits in a tiny brain: new approaches for understanding the neural circuitry of *Drosophila*. Trends in Neurosciences 2008, 31 (10), 512-520.

Ovsepian, Saak V., et al. "Pushing the boundaries of neuroimaging with optoacoustics." Neuron 96.5 (2017): 966-988.

Papadopoulos, O. Simandoux, S. Farahi, J. Pierre Huignard, E. Bossy, D. Psaltis, and C. Moser, "Optical-resolution photoacoustic microscopy by use of a multimode fiber," Appl. Phys. Lett. 102, 211106 (2013).

Papadopoulos, S. Farahi, C. Moser, and D. Psaltis, "Highresolution, lensless endoscope based on digital scanning through a multimode optical fiber," Biomed optics express 4, 260-270 (2013).

Patil, Ujwal, et al. "In vitro/in vivo toxicity evaluation and quantification of iron oxide nanoparticles." International journal of molecular sciences 16.10 (2015): 24417-24450.

Pisanello, F.; Sileo, L.; Oldenburg, I.A.; Pisanello, M.; Martiradonna, L.; Assad, J. A.; Sabatini, B.L.; De Vittorio, M., Multipoint-Emitting Optical Fibers for Spatially Addressable In Vivo Optogenetics. Neuron 2014, 82 (6), 1245-1254.

Richter, D. W.; Pierrefiche, O.; Lalley, P. M.; Polder, H. R., Voltage-clamp analysis of neurons within deep layers of the brain. J. Neurosci. Methods 1996, 67 (2), 121-131.

Rose, G. J.; Alluri, R. K.; Vasquez-Opazo, G. A.; Odom, S. E.; Graham, J. A.; Leary, C. J., Combining pharmacology and whole-cell patch recording from CNS neurons, in vivo. J. Neurosci. Methods 2013, 213 (1), 99-104.

Saiki, T.; Matsuda, K., Near-field optical fiber probe optimized for illumination-collection hybrid mode operation. Applied Physics Letters 1999, 74 (19), 2773-2775.

Schneider, D. M.; Nelson, A.; Mooney, R., A synaptic and circuit basis for corollary discharge in the auditory cortex. Nature 2014, 513 (7517), 189-+.

Sethuraman, S. R. Aglyamov, J. H. Amirian, R. W. Smalling, and S. Y. Emelianov, "Intravascular photoacoustic imaging using an ivus imaging catheter," IEEE transactions on ultrasonics, ferroelectrics, frequency control 54 (2007).

Shi, K. Ito, L. Ma, T. Yoshida, Y. Matsuura, and M. Miyagi, "Fabrication of a polymer-coated silver hollow optical fiber with high performance," Appl. optics 45, 6736-6740 (2006).

Shung, J. Cannata, and Q. Zhou, "Piezoelectric materials for high frequency medical imaging applications: A review," J. Electroceramics 19, 141-147 (2007).

Simandoux, N. Stasio, J. Gateau, J.-P. Huignard, C. Moser, D. Psaltis, and E. Bossy, "Optical-resolution photoacoustic imaging through thick tissue with a thin capillary as a dual optical-in acousticout waveguide," Appl. Phys. Lett. 106, 094102 (2015).

Smetters, D.; Majewska, A.; Yuste, R., Detecting action potentials in neuronal populations with calcium imaging. Methods—a Companion to Methods in Enzymology 1999, 18 (2), 215-221.

Smith, A Shah, Yong-Kyun Lee, B O'Brien, D Kullman, A Sridharan, J Muthuswamy, J B Christen "Optogenetic Neurostimulation of the Auricular Vagus using Flexible OLED Display Technology to Treat Chronic Inflammatory Disease and Mental Health Disorders" Electronics Letters, DOI: 10.1049/el.2015.3450, 2016.

So, P. T. C.; Dong, C. Y.; Masters, B. R.; Berland, K. M., Two-photon excitation fluorescence microscopy. Annual Review of Biomedical Engineering 2000, 2, 399-429.

Stasio, A. Shibukawa, I. N. Papadopoulos, S. Farahi, O. Simandoux, J.-P. Huignard, E. Bossy, C. Moser, and D. Psaltis, "Towards new applications using capillary waveguides," Biomed. optics express 6, 4619-4631 (2015).

Stern, E. A.; Kalman, Z.; Lewis, A.; Lieberman, K., simple method for focusing x-rays using tapered capillaries. Applied Optics 1988, 27 (24), 5135-5139.

Stosiek, C.; Garaschuk, O.; Holthoff, K.; Konnerth, A., In vivo two-photon calcium imaging of neuronal networks. Proc. Natl. Acad. Sci. U. S. A. 2003, 100 (12), 7319-7324.

Strohm, E. M.; Moore, M. J.; Kolios, M. C., Single Cell Photoacoustic Microscopy: A Review, Ieee Journal of Selected Topics in Quantum Electronics 2016, 22 (3).

Stuart, G. J.; Dodt, H. U.; Sakmann, B., patch-clamp recordings from the soma and dendrites of neurons in brain-slices using infrared video microscopy. Pflugers Arch. 1993, 423 (5-6), 511-518.

Suk, I. van Welie, S. B. Kodandaramaiah, B. Allen, C. R. Forest, and E. S. Boyden, "Closed-loop real-time imaging enables fully automated cell-targeted patch-clamp neural recording in vivo," Neuron. 95, 1037-1047 (2017).

Svoboda, K.; Yasuda, R., Principles of two-photon excitation microscopy and its applications to neuroscience. Neuron 2006, 50 (6), 823-839.

Timofeev, I.; Grenier, F.; Steriade, M., Disfacilitation and active inhibition in the neocortex during the natural sleep-wake cycle: An intracellular study. Proc. Natl. Acad. Sci. U. S. A. 2001, 98 (4), 1924-1929.

Freudenrich, C. How Fiber Optics Work. Mar. 6, 2001, HowStuffWorks. com, pp. 1-9 (Year: 2001).

\* cited by examiner

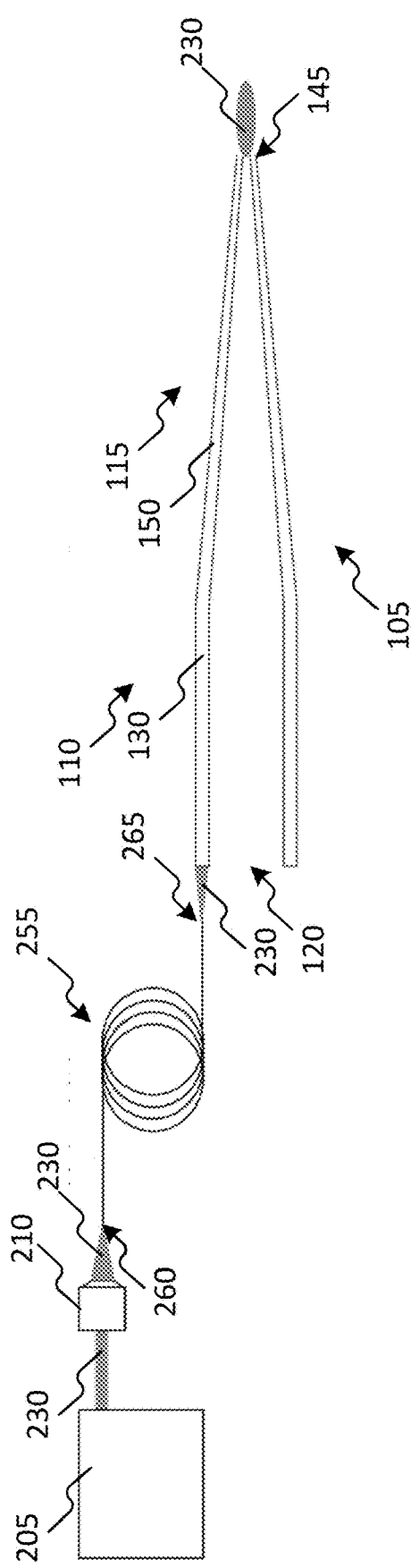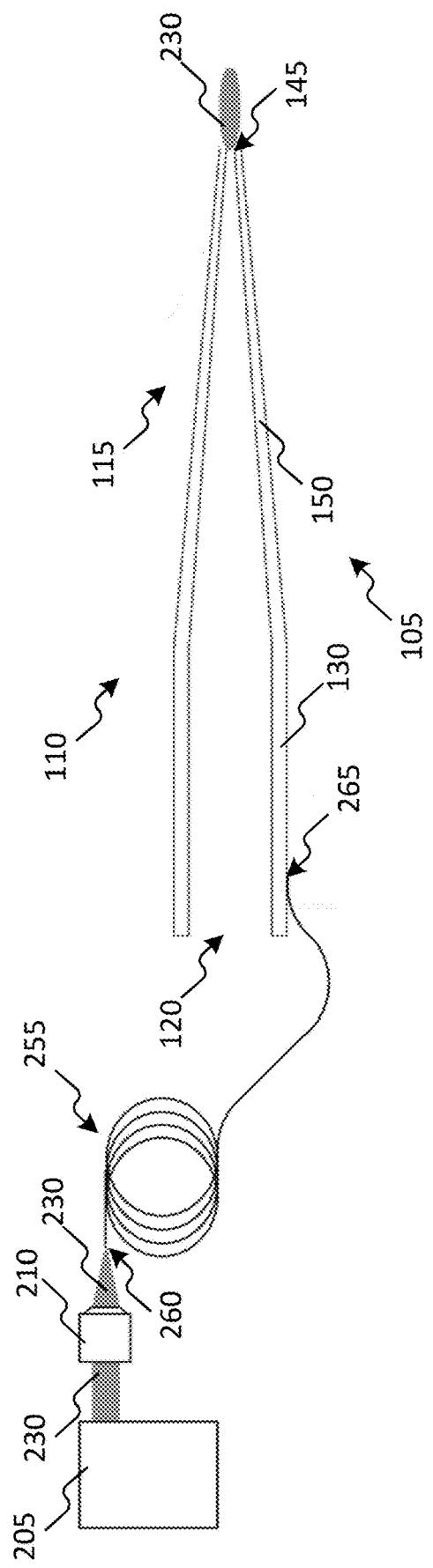

PHOTOACOUSTIC TARGETING WITH MICROPIPETTE ELECTRODES

CROSS-REFERENCE TO RELATED APPLICATIONS

This application is a non-provisional of and claims benefit of U.S. Provisional Application No. 62/572,338, filed on Oct. 13, 2017, the entire contents of which are incorporated herein by reference.

BACKGROUND

Intracellular single-unit recordings of neurons can be performed by piercing the membrane of the neuron using a microelectrode. This procedure is typically performed under a microscope, however this is not always feasible with in vivo recordings where there may be layers of tissue covering the neuron. In these situations, and often with in vitro recordings, the electrode must be blindly inserted repeatedly into tissue while monitoring the voltage at the electrode tip. This method is highly inefficient and lengthens the amount of time it takes to run tests. This method also heavily relies on the abilities of the individual performing the test resulting in issues in reproducibility.

SUMMARY

By taking advantage of the photoacoustic effect and the unique absorption curve of DNA, an electrode tip can be guided towards a neuron to increase the probability of successfully inserting the electrode tip into the neuron, or simply placing the electrode tip near the neuron in the case of extracellular recordings.

Thus, the disclosure provides a photoacoustic targeting system. In one embodiment, the photoacoustic targeting system includes a light source, a micropipette electrode, an acoustic transducer, and a controller. The light source is configured to emit pulsed light. The micropipette electrode is configured to deliver the pulsed light to a target cell. The acoustic transducer is configured to receive photoacoustic signals generated due to optical absorption of light energy by the target cell. The controller is configured to determine a position of the micropipette electrode relative to the target cell based on the photoacoustic signals.

The disclosure also provides a photoacoustic targeting system. In one embodiment, the photoacoustic targeting system includes a micropipette electrode, a light source, a right angle prism, an acoustic transducer, and a controller. The micropipette electrode includes a tip and a body. The tip is positioned proximate to or at least partially within a target cell. The body is attached to the tip. The light source is configured to emit pulsed light. The right angle prism is positioned within the micropipette electrode and relative to the light source such that the pulsed light enters the right angle prism at a first non-hypotenuse face of the right angle prism. The right angle prism is also positioned within the micropipette electrode and relative to the light source such that the pulsed light reflects off of a hypotenuse face of the right angle prism. The right angle prism is further positioned within the micropipette electrode and relative to the light source such that the pulsed light exits the right angle prism at a second non-hypotenuse face of the right angle prism along a trajectory toward the tip of the micropipette electrode. The acoustic transducer is configured to receive photoacoustic signals generated due to optical absorption of light energy by the target cell. The controller is configured to determine a position of the micropipette electrode relative to the target cell based on the photoacoustic signals.

Other aspects of the invention will become apparent by consideration of the detailed description and accompanying drawings.

BRIEF DESCRIPTION OF THE DRAWINGS

FIG. 5 is a diagram of a photoacoustic targeting system that includes an optical fiber, in accordance with some embodiments.

FIG. 6 is a diagram of a photoacoustic targeting system that includes an optical fiber fused to a micropipette electrode, in accordance with some embodiments.

DETAILED DESCRIPTION

Figure 1:
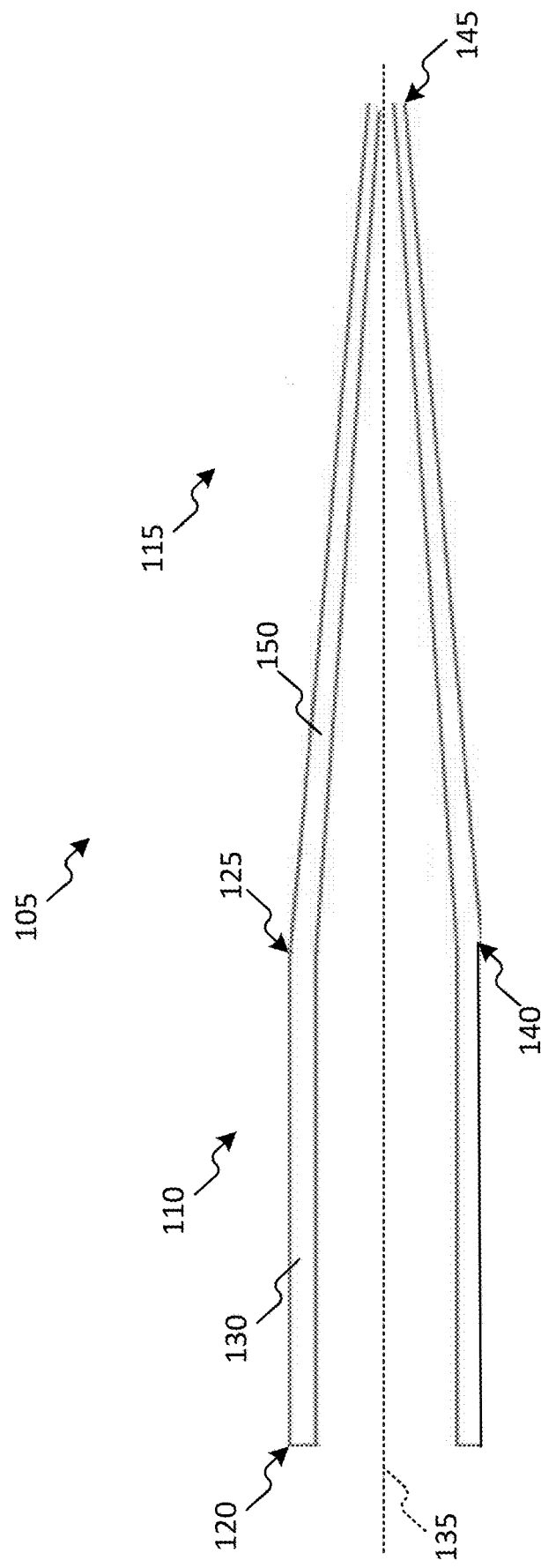
FIG. 1 is a diagram of a microelectrode pipette, in accordance with some embodiments.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Glass micropipette electrodes are a powerful tool for providing electrophysiological recordings of neuronal activity within both in vitro and in vivo biological systems. This fundamental information has enabled a better understanding of neuronal activity, indicative of cell and network function.

However, inherent system complexity leads to difficulties in successfully and accurately acquiring cellular recordings, mainly dependent on the skill of the user. These recordings are often done with either a sharp or patch micropipette. A typical sharp micropipette will have a tip diameter that approaches or exceeds the limit of resolution of most optical microscopes. Thus, this technique, although performed under high optical magnification, is carried out without knowledge of the exact location of the micropipette tip, relative to the neuron. This makes it difficult to successfully target the neuron and acquire recordings with high efficiency. Patch micropipettes, used to perform traditional patch clamping, have a tip diameter larger than sharp micropipettes, on the scale of a few microns. The larger tip size allows for the patch micropipette to be more readily and accurately positioned near the intended target. Lack of real-time feedback regarding neuronal movement often results in a poor gigaohm seal. Previous systems and techniques designed to increase the successful acquisition of intracellular recordings: (i) suffer from low success rates, (ii) depend strongly on the skill of the electrophysiologist, (iii) rely heavily on cell labeling, or (iv) are limited by the penetration depth of light. Imaging based approaches have led to increased rates of successful recordings, but are not without drawbacks. The reliance on optical microscopy ensures that these techniques will not be effective for locating neurons that are beyond the penetration depth of light. Moreover, utilizing fluorescence requires expensive reagents and specialized infrastructure. To address these issues, this disclosure introduces targeting approaches that incorporate a photoacoustic feedback system with micropipette electrodes. The targeting approaches disclosed herein enable increased rates of successful neuronal recordings, without the need for exogenous contrast agents. The targeting approaches disclosed utilize the photoacoustic effect. In brief, this phenomenon is defined by ultrasound waves produced by small thermal expansions, caused by optical absorption. This enables detection of particular absorbers through the use of specific wavelengths that match their peak optical absorbance. DNA and RNA have a strong absorption peak in the UV range, and thus can serve as endogenous chromophores. These absorption peaks can be used to create image reconstructions of cellular and tissue structures using photoacoustic microscopy (PAM).

This imaging technique can be performed by concentrating light to a small spot size, which can then be used to generate the photoacoustic effect at specific spatial locations. One method of concentrating light is through the use of an optical waveguide, which tapers down to a small diameter. Light is able to travel down the length of the waveguide. Immediately upon exiting the tip, the light is the same diameter as the waveguide, before increasing in diameter. Glass micropipette electrodes, due to their material properties (i.e., borosilicate glass and quartz glass), can be used as hollow optical waveguides. With minor adjustments, light coupled to the glass wall can be efficiently guided down the length of the micropipette electrode and out of the tip. The properties of the sound generated by the light traveling along the micropipette can reveal information regarding the presence of a particular absorber along the path of the micropipette, and its spatial location, relative to the tip of the device. This enables a photoacoustic feedback system that can be used to move the micropipette toward a particular absorber.

FIG. 1 is a diagram of one example embodiment of a micropipette electrode 105. In the embodiment illustrated, the micropipette electrode 105 includes a body 110 and a tip 115. The tip 115 is attached to the body 110. In some embodiments, the body 110 has a generally tubular shape. The body 110 includes a first end 120 and a second end 125 opposite the first end 120. The first end 120 is distal to the tip 115. The second end 125 is proximal to the tip 115. The body 110 also includes a first sidewall 130 that extends along a longitudinal axis 135 of the micropipette electrode 105 from the first end 120 to the second end 125. In some embodiments, an inner diameter of the body 110 is approximately 0.75 millimeters. In some embodiments, the tip 115 is generally tubular shaped. The tip 115 includes a third end 140 and a fourth end 145. The third end 140 of the tip 115 is proximal to the second end 125 of the body 110. The fourth end 145 of the tip 115 is distal to the body 110. The tip 115 also includes a second sidewall 150 that extends along the longitudinal axis 135 of the micropipette electrode 105 from the third end 140 to the fourth end 145. The second sidewall 150 is tapered along the longitudinal axis 135 from the third end 140 to the fourth end 145. In some embodiments, an inner diameter of the tip 115 at the fourth end 145 is approximately 3.5 micrometers.

Figure 2:
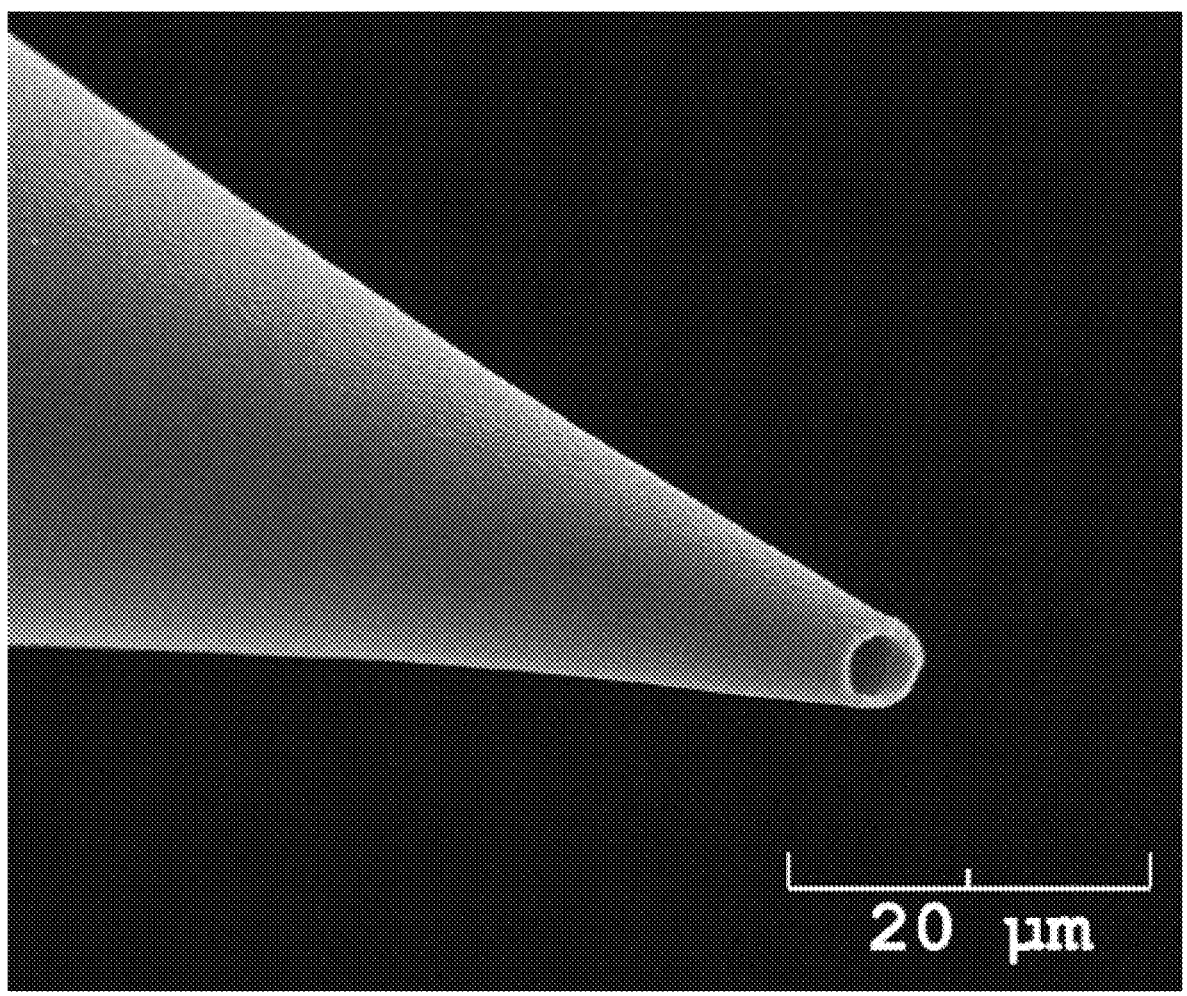
FIG. 2 is an image of a tip of a microelectrode pipette with a metallic coating, in accordance with the some embodiments.

In some embodiments, the first sidewall 130 and the second sidewall 150 comprise glass (for example, borosilicate glass or quartz glass). In order to facilitate the propagation of light (or pulsed light) along the first sidewall 130 and the second sidewall 150, in some embodiments, the first sidewall 130 and the second sidewall 150 are coated with a metallic layer (for example, an aluminum coating). In some embodiments, the metallic layer is approximately 200 nanometers thick. In some embodiments, the thickness of the metallic layer is determined using a reference piezo sensor during the deposition process. FIG. 2 is scanning electron microscopy image of an example tip that is coated with the metallic layer. As shown in FIG. 2, the metallic layers forms smooth and continuous coating on the outer surface of the micropipette electrode 105.

Figure 3:
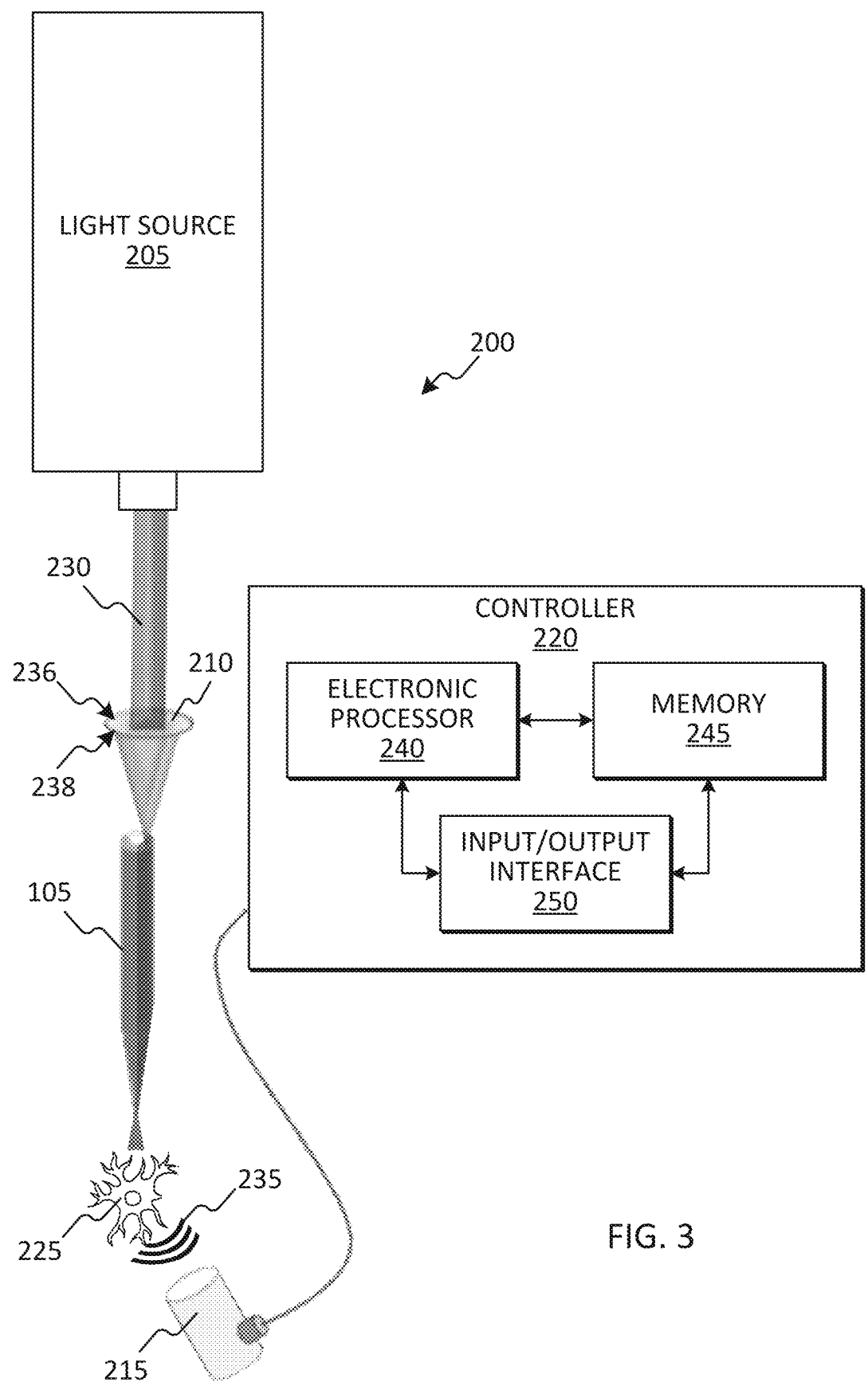
FIG. 3 is a diagram of a photoacoustic targeting system, in accordance with some embodiments.

FIG. 3 is a diagram of one example embodiment of a photoacoustic targeting system 200. In the embodiment illustrated in FIG. 3, the photoacoustic targeting system 300 includes the micropipette electrode 105, a light source 205, a lens 210, an acoustic transducer 215, and a controller 220. In the embodiment illustrated in FIG. 3, the tip 115 of micropipette electrode 105 is positioned proximate to a target cell 225 (for example, a neuron). Alternatively or in addition, the tip 115 of micropipette electrode 105 is positioned at least partially within the target cell 225. As will be described in more detail below, the micropipette electrode 105 acts as a light guide to deliver pulsed light 230 emitted by the light source 205 to the target cell 225. The controller 220 determines a position of the tip 115 of the micropipette electrode 105 relative to the target cell 225 based on photoacoustic signals 235 received by the acoustic transducer 215 that are generated due to optical absorption of light energy by the target cell 225.

The light source 205 is configured to emit pulsed light 230 as the excitation source to induce photoacoustic signals. In some embodiments, the light source 205 is a laser (for example, a tunable LS-2134-LT40 Nd:YAG/Ti:Sapphire nanosecond pulsed laser by Symphotic TII Corporation). In some embodiments, the light source 205 emits pulsed light with a 460 nanometer wavelength. In some embodiments, the light source 205 provides an excitation light with a full width half maximum (FWHM) of 12 to 15 nanoseconds at a pulse repetition rate of 10 Hertz. In some embodiments, the light source 205 emits a 20 micron spot of pulsed light 230 at 1 centimeter away from the target cell 225.

Figure 4:
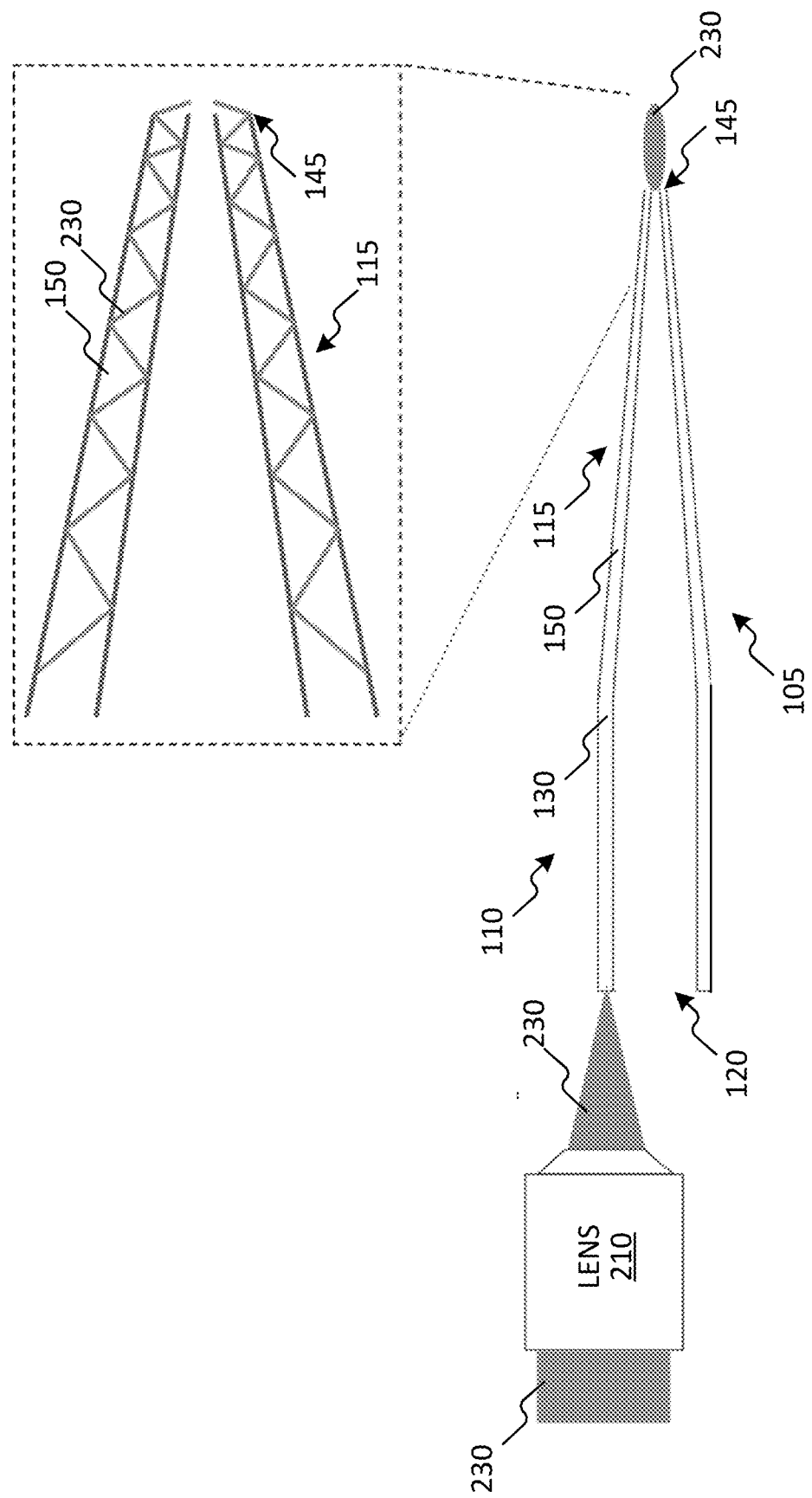
FIG. 4 is a diagram of a lens and a micropipette electrode included in the photoacoustic targeting system of FIG. 3, in accordance with some embodiments.

Having a concentrated spot size increases the photoacoustic effect at that location relative to the surrounding volume. To that end, the lens 210 is configured to reduce a beam width of the pulsed light 230. The lens 210 includes a receiving face 236 this is positioned relative to the light source 205 to receive the pulsed light 230. The lens 210 also includes an emitting face 238 that is positioned relative to the micropipette electrode 105 such that the pulsed light 230 exiting the lens 210 enters the micropipette electrode 105. In some embodiments, the lens 210 is an achromatic doublet lens (for example, an achromatic doublet lens ACN127-050-A by Thorlabs). In the embodiment illustrated in FIG. 3, the lens 210 focuses the pulsed light 230 into the micropipette electrode 105. FIG. 4 is provided to illustrate one example embodiment of the focusing of the pulsed light 230 into the micropipette electrode 105. As illustrated in FIG. 4, the lens 210 reduces the beam width of the pulsed light 230 to focus the pulsed light 230 into the first sidewall 130 of the first end 120 of the body 110 of the micropipette electrode 105. The pulsed light 230 travels through the first sidewall 130 of the body 110 and through the second sidewall 150 of the tip 115. The pulsed light 230 exits the micropipette electrode 105 at the fourth end 145 of the tip 115.

Returning to FIG. 3, in some embodiments, the acoustic transducer 215 is placed in the medium that the electrode reading is taking place. Alternatively of in addition, the acoustic transducer 215 is placed on the surface of the animal or person being probed. The acoustic transducer 215 receives photoacoustic signals 235 generated due to optical absorption of light energy by the target cell 225. In some embodiments, the acoustic transducer 215 includes a 50 Megahertz transducer with an element diameter of 6 millimeters, and a −6 decibels fractional bandwidth of 82% (for example, a V214-BB-RM transducer by Olympus).

The acoustic transducer 215 is coupled to the controller 220. The photoacoustic signals 235 detected by the acoustic transducer 215 are sent to the controller 220. In the embodiment illustrated in FIG. 3, the controller 220 includes an electronic processor 240 (for example, a microprocessor), memory 245, an input/output interface 250, and a bus. In alternate embodiments, the controller 220 may include fewer or additional components in configurations different from the configuration illustrated in FIG. 3. The bus connects various components of the controller 220 including the memory 245 to the electronic processor 240. The memory 245 includes read only memory (ROM), random access memory (RAM), an electrically erasable programmable read-only memory (EEPROM), other non-transitory computer-readable media, or a combination thereof. The electronic processor 240 is configured to retrieve program instructions and data from the memory 245 and execute, among other things, instructions to perform the methods described herein. Alternatively, or in addition to, the memory 245 is included in the electronic processor 240. The input/output interface 250 includes routines for transferring information between components within the controller 220 and other components of the photoacoustic targeting system 200, as well as components external to the photoacoustic targeting system 200. The input/output interface 250 is configured to transmit and receive signals via wires, fiber, wirelessly, or a combination thereof. Signals may include, for example, information, data, serial data, data packets, analog signals, or a combination thereof The controller 220 is configured to determine a position of the micropipette electrode 105 relative to the target cell 225 based on the photoacoustic signals 235 received by the acoustic transducer 215. As the tip 115 of the micropipette electrode 105 gets close to the target cell 225, the photoacoustic signals 235 from the photoacoustic effect will increase. This provides feedback to the controller 220 as to the relative location of the tip 115 of the micropipette electrode 105 with respect to the target cell 225. In some embodiments, the controller 220 performs pre-processing (for example, amplifying and filtering) on the photoacoustic signals 235. In one example embodiment, the photoacoustic signals 235 are amplified using a 59 decibel gain and filtered with a 1 megahertz high pass filter.

In some embodiments, the controller 220 is coupled to the light source 205. In some embodiments, the controller 220 adjusts the modulation of the pulsed light 230 emitted by the light source 205 to guide the tip 115 of the micropipette electrode 105 to the target cell 225. The controller 220 may set the energy of the light source 205 to be proportional to the detection volume at the tip 115 of the micropipette electrode 105. Once the target cell 225 is detected to be within a predetermined distance of the tip 115, the power of the light source 205 is dropped to decrease the detection volume, which requires the micropipette electrode 105 to move toward the target cell 225 to increase the photoacoustic signals 235. This energy modulation process can be repeated several times until the distance between the target cell 225 and tip 115 of the micropipette electrode 105 is less than a predetermined distance threshold.

The beam shape of the pulsed light 230 exiting the tip 115 of the micropipette electrode 105 depends on several factors. One example factor is the angle of incidence of the pulsed light 230. Large angles of incidence can result in poor transmission of the pulsed light 230 along the entire length of the micropipette electrode 105. In order to ensure maximum light transmission, in some embodiments, the pulsed light 230 is coupled to the micropipette electrode 105 with a near zero angle of incidence.

In some embodiments, the photoacoustic targeting system 200 includes an optical fiber 255 as illustrated in FIG. 5. The optical fiber 255 includes fifth end 260 and a sixth end 265. In the embodiment illustrated in FIG. 5, the fifth end 260 of the optical fiber 255 is positioned relative to the lens 210 to receive the pulsed light 230. Further, the sixth end 265 of the optical fiber 255 is positioned relative to the micropipette electrode 105 such that the pulsed light 230 exiting the sixth end 265 of the optical fiber 255 enters the first sidewall 130 at the first end 120 of the body 110 of the micropipette electrode 105. FIG. 6 is an example embodiment in which the sixth end 265 of the optical fiber 255 is fused to the first sidewall 130 of the body 110 of the micropipette electrode 105.

Figure 7:
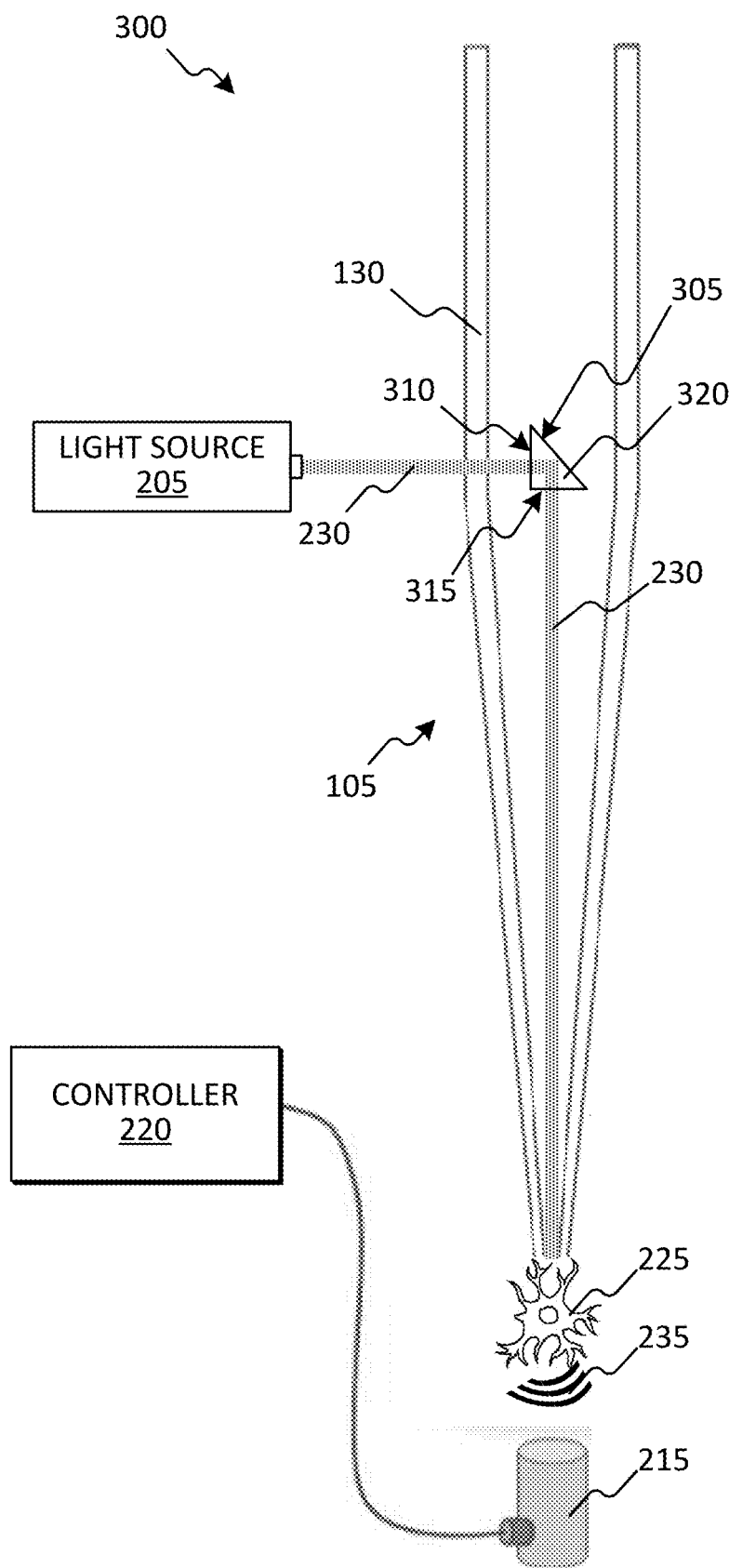
FIG. 7 is a diagram of a photoacoustic targeting system that includes a right angle prism within a micropipette electrode, in accordance with some embodiments.

FIG. 7 is a diagram of one example embodiment of a photoacoustic targeting system 300 in which a right angle prism 305 is inserted into the micropipette electrode 105. The photoacoustic targeting system 300 illustrated in FIG. 7 includes the micropipette electrode 105, the right angle prism 305, the light source 205, the acoustic transducer 215, and the controller 220. In the embodiment illustrated in FIG. 7, the right angle prism 305 is positioned where the micropipette electrode 105 begins to taper to a fine point. In other words, the right angle prism 305 is positioned proximate to the third end 140 of the tip 115. The right angle prism 305 includes a first non-hypotenuse face 310, a second non-hypotenuse face 315, and a hypotenuse face 320. The right angle prism 305 is positioned such that second non-hypotenuse face 315 has its normal pointing down an axis of the micropipette electrode 105 toward the fourth end 145 of the tip 115. The first non-hypotenuse face 310 has its normal pointing perpendicular to the axis of the micropipette electrode 105. As illustrated in FIG. 7, the light source 205 emits pulsed light 230 toward the first non-hypotenuse face 310 of the right angle prism 305. The pulsed light 230 passes through the first sidewall 130 of the micropipette electrode 105 and enters the right angle prism 305 at the first non-hypotenuse face 310. The pulsed light 230 reflects off the hypotenuse face 320 at a substantially ninety degree angle and then exits the right angle prism 305 at the second non-hypotenuse side 315. The pulsed light 230 travels along a trajectory toward the fourth end 145 of the tip 115, exits the micropipette electrode 105, and is delivered to the target cell 225. In other words, the pulsed light 230 enters the right angle prism 305 along a first trajectory, and exits the right angle prism 305 along a second trajectory. In some embodiments, the reflection angle between the first trajectory and the second trajectory is substantially ninety degrees.

Figure 8:
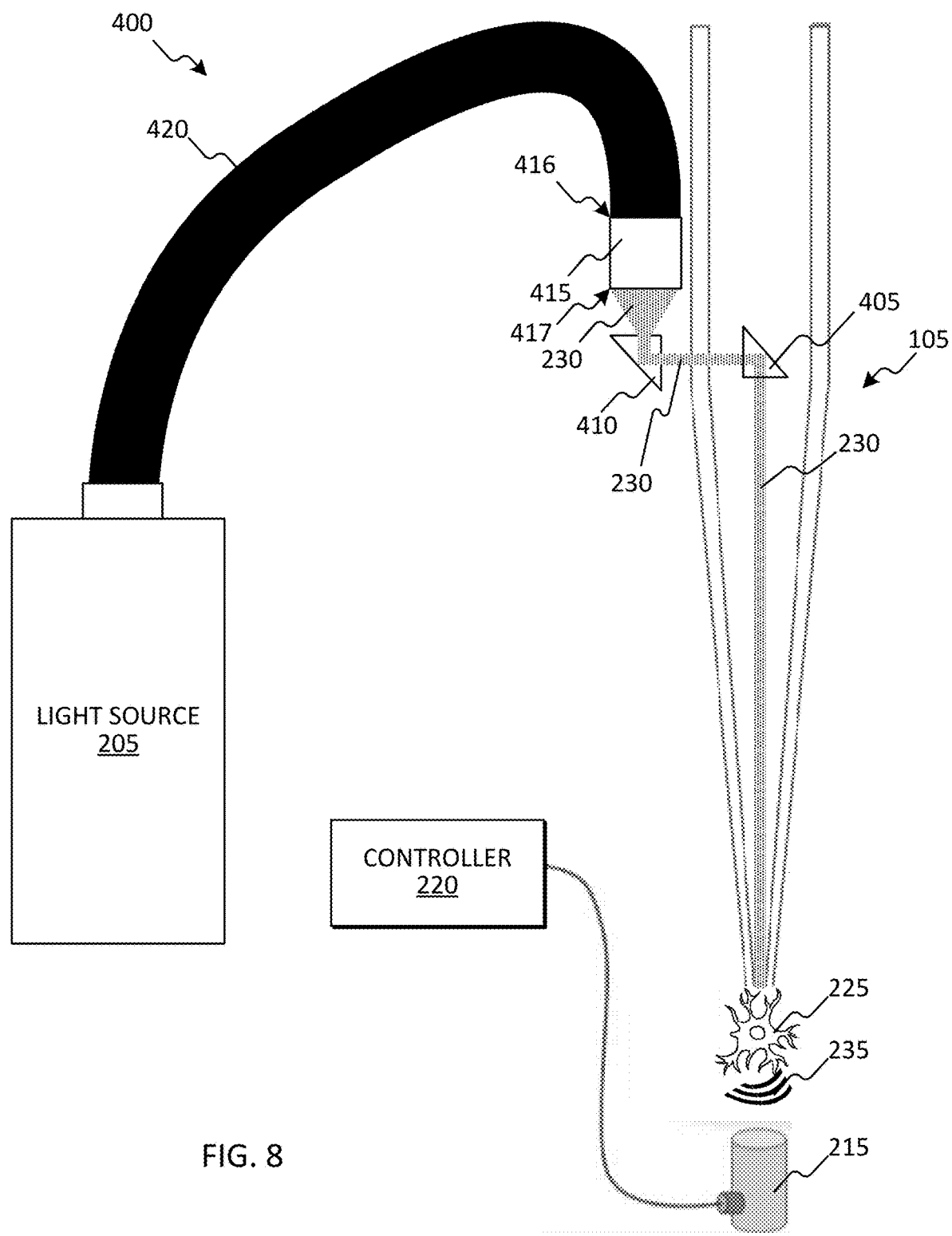
FIG. 8 is a diagram of a photoacoustic targeting system that includes two right angle prisms, in accordance with some embodiments.

Different types of lenses can be used such that the pulsed light 230 entering the right angle prism 305 is converging down to a micron sized point. In some embodiments, a lens may be selected based on the diameter of the tip 115 such that pulsed light 230 becomes concentrated at the tip 115 of the micropipette electrode 105. FIG. 8 is a diagram of one example embodiment of a photoacoustic targeting system 400 including the micropipette electrode 105, a first right angle prism 405, a second right angle prism 410, a lens 415, an optical fiber 420, the light source 205, the acoustic transducer 215, and the controller 220. In the embodiment illustrated in FIG. 8, pulsed light 230 emitted by the light source 205 passes though the optical fiber 420, and exit into the lens 415. The lens 415 is configured to reduce a beam width of the pulsed light 230. The lens 415 includes a receiving face 416 this is positioned relative to the optical fiber 420 to receive the pulsed light 230. The lens 415 also includes an emitting face 417 that is positioned relative to second right angle prism 410 such that the pulsed light 230 exiting the lens 415 enters the second right angle prism 410. In some embodiments, the lens 415 is a grin lens. In some embodiments, the lens 415 is selected such that the pulsed light 230 that exits the lens 415 becomes concentrated to a micron level spot, some distance away from the emitting face 417 of the lens 415. Attached to the emitting face 417 of the lens 415, is the second right angle prism 410 which redirects the pulsed light 230 in a substantially ninety degree angle towards the first right angle prism 405 inside the micropipette electrode 105. The pulsed light 230, already on a converging path, is redirected again by the first right angle prism 405 inside the micropipette electrode 105, toward the fourth end 145 of the tip 115 of the micropipette electrode 105.

Figure 9:
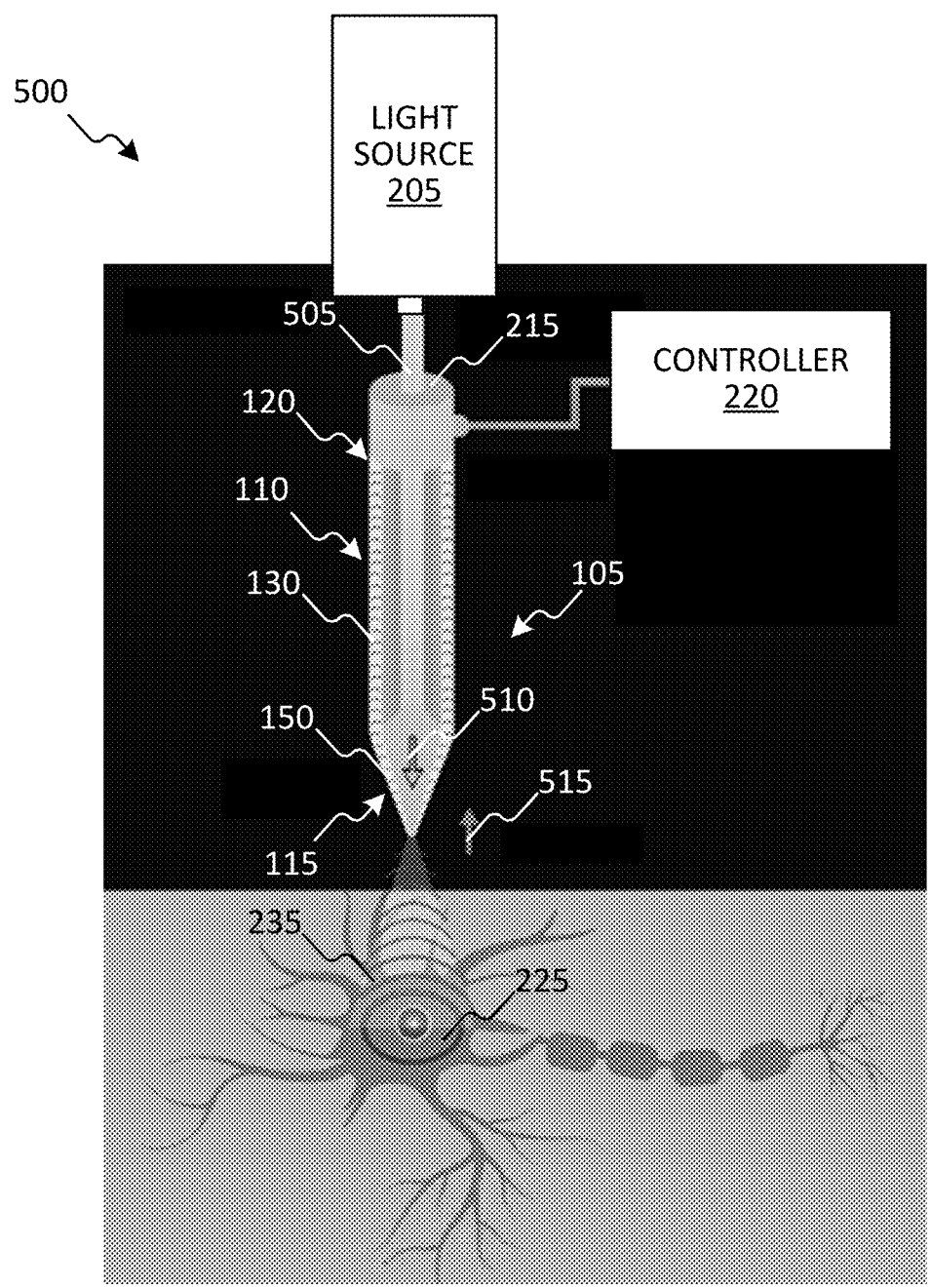
FIG. 9 is a diagram of a photoacoustic targeting system that includes an optical fiber partially positioned within a micropipette electrode, in accordance with some embodiments.

FIG. 9 is a diagram of one example embodiment of a photoacoustic targeting system 500 including the micropipette electrode 105, the light source 205, the acoustic transducer 215, the controller 220, and an optical fiber 505. In the embodiment illustrated in FIG. 9, a portion of the optical fiber 505 is disposed inside the micropipette electrode 105. The pulsed light emitted by the light source 205 passes though the optical fiber 505 and exits into the tip 115 of the micropipette electrode 105 (generally in the direction of arrow 510). The optical absorption of light energy by the target cell 225 generates photoacoustic signals 235 which reflect back to the micropipette electrode 105 (generally in the direction of arrow 515). The photoacoustic signals 235 pass through the second sidewall 150 of the tip 115 and the first sidewall 130 of the body 110 and are received by the acoustic transducer 215. In the embodiment illustrated in FIG. 9, the acoustic transducer 215 is positioned proximate to the first end 120 of the body 110 of the micropipette electrode 105.

Fluorescence microscopy in its most basic form consists of providing a dye or stain with an excitation light of a specific wavelength and the dye or stain absorbs that light and emits light at a different specific wavelength. In some embodiments, the target cell 225 (in vivo or in vitro) can be stained with any common stain or dye. The pulsed light 230 is introduced as is the excitation light for inducing the photoacoustic effect, however the emission light from the dye or stain returns back up the tip 115 of the micropipette electrode 105 towards the first right angle prism 405 inside the micropipette electrode 105, is redirected outward to the second right angle prism 410, and is redirected back through the lens 415.

The implementations and processes of the invention will be better understood by reference to the following examples, which are intended as an illustration of and not a limitation upon the scope of the invention.

EXAMPLES

Example 1

250 Micrometer Diameter Carbon Fiber Rod with Varying Step Sizes

Figure 10A:
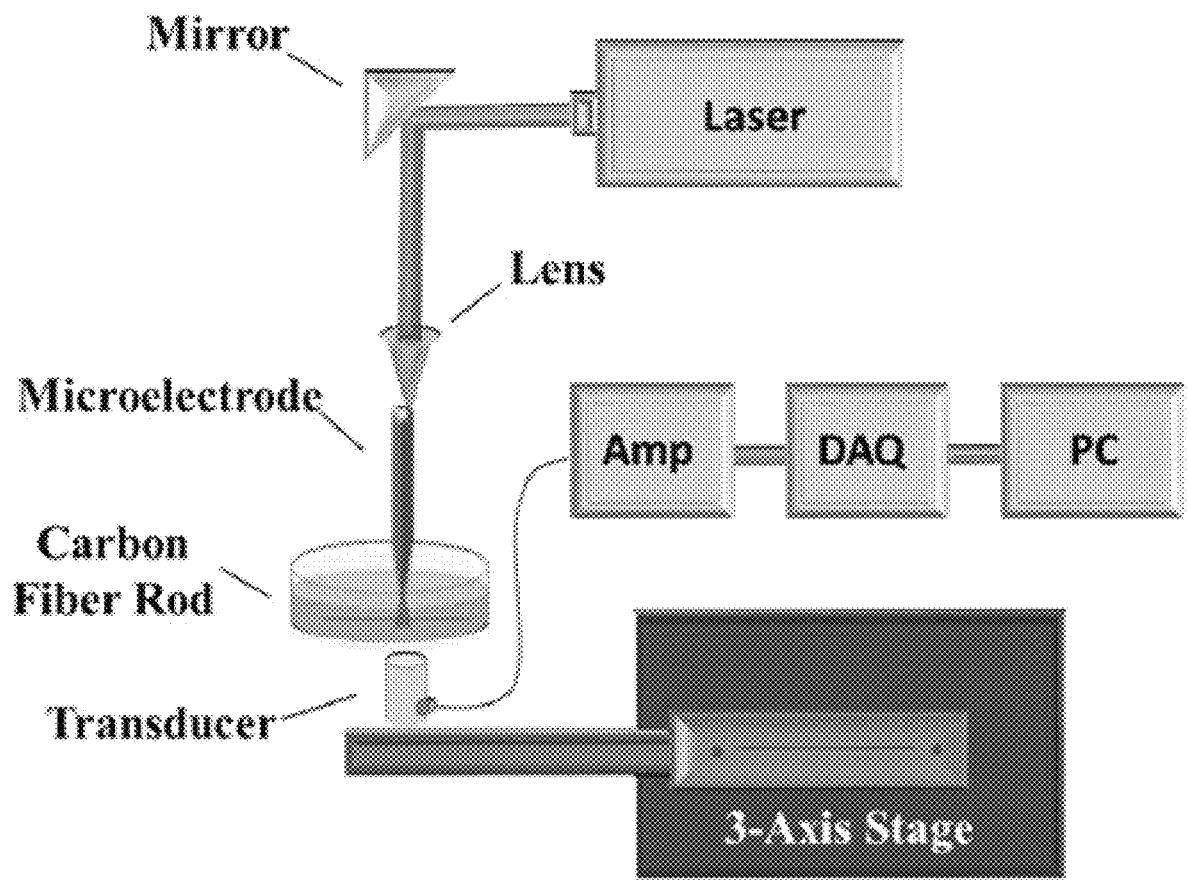
FIG. 10A is a diagram of an example experimental setup for testing a micropipette electrode.
Figure 10B:
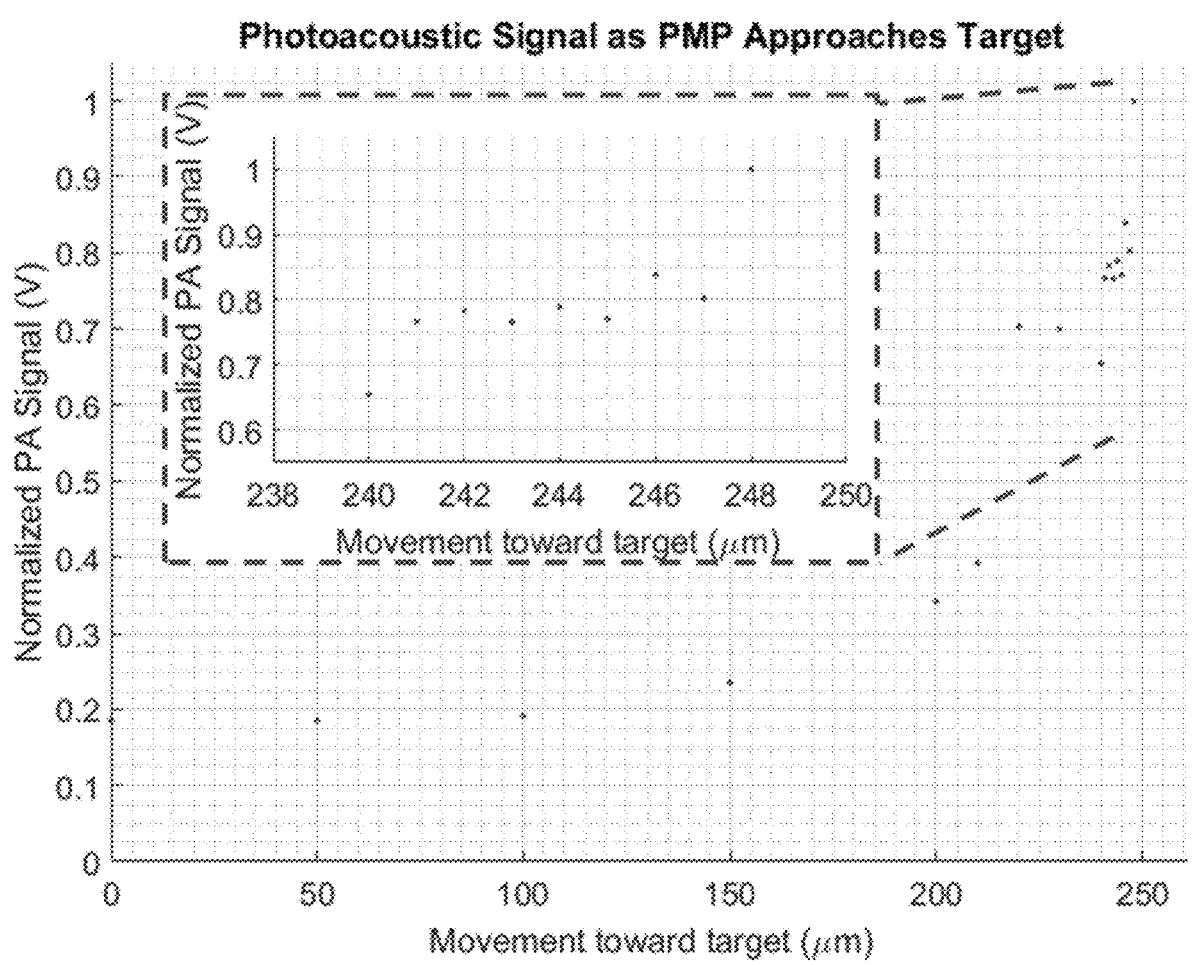
FIG. 10B is a graph of photoacoustic signals generated by a 250 micrometer line target.

FIG. 10A is a schematic representation of the example experimental setup that was used to evaluate the capacity of a micropipette electrode to induce the photoacoustic effect. A 250 micrometer diameter carbon fiber rod was submerged in distilled water within a small petri dish, under which a transducer was positioned. The position of the petri dish was controlled by a three-axis motorized stage. The stage moved horizontally in a direction perpendicular to the orientation of the target in 2.5 micrometer steps. The vertical position of the micropipette electrode, above the petri dish, allowed the target to cross paths with the micropipette electrode during horizontal movement. A laser exiting the micropipette electrode induced a photoacoustic signal, detected by the transducer positioned directly below the petri dish. The stage was then used to move the petri dish vertically toward the micropipette electrode in varying step sizes. As the photoacoustic target approached or receded from the micropipette electrode tip, a corresponding increased or decreased photoacoustic signal was generated, as shown in FIG. 10B. Initially, the stage was moved vertically toward the micropipette electrode in 50 micrometer steps until a noticeable increase in photoacoustic signal was detected, at which point the step size was decreased to 10 micrometers. After multiple 10 micrometer steps, the step size was further decreased to 1 micrometer steps. The embedded graph in FIG. 10B highlights the increase in photoacoustic signal after each 1 micrometer step. These results identify the ability of the micropipette electrode to vertically approach targets through guided signal intensity.

Example 2

250 Micrometer Diameter Carbon Fiber Rod with 2.5 Micrometer Steps

Figure 11A:
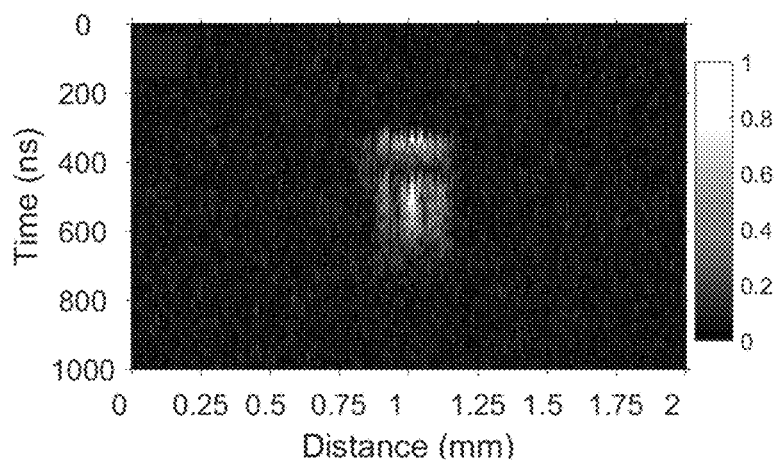
FIG. 11A is a photoacoustic image reconstruction of a 250 micrometer carbon fiber rod line target.
Figure 11B:
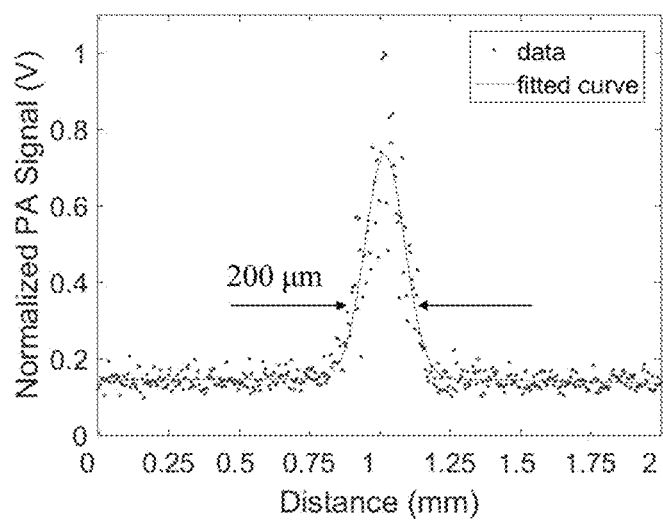
FIG. 11B is a graph of maximum photoacoustic signals at different horizontal steps for a 250 micrometer line target.
Figure 11C:
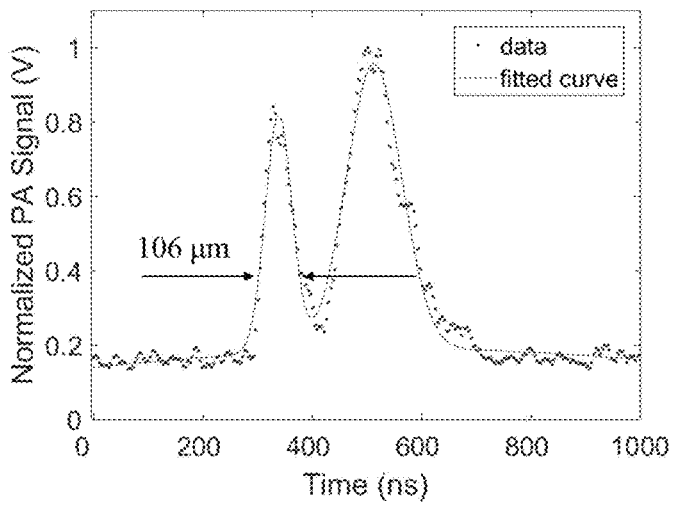
FIG. 11C is a graph of maximum photoacoustic signals at different vertical steps for a 250 micrometer line target.

A 250 micrometer diameter carbon fiber rod was used as a line target in the example experimental setup depicted in FIG. 10A. The target was submerged in distilled water within a small petri dish container. The three-axis motorized stage was used to move the target horizontally in 2.5 micrometer steps. At each step, a laser was fired down the micropipette electrode and 1,000 nanoseconds of data from the resulting photoacoustic signal was acquired. A Hilbert Transform was applied to the data and the complex magnitude was subsequently calculated, normalized, and converted into a series of pixel values. This data is shown in FIG. 11A as a photoacoustic image reconstruction of the 250 micrometer line target. The maximum signal at each horizontal step for the 250 micrometer line target is shown in FIG. 11B. Using a Gaussian fit, the measured transverse full width half maximum of the 250 micrometer line target was 200 micrometers. This indicated that the resulting photoacoustic image was clearly indicative of the size of the target. A maximum signal generated along the vertical direction for the line target is displayed in FIG. 11C. Measuring the full width half maximum using a Gaussian fit and a speed of sound of 1,498 meters per second resulted in a value of 106 micrometers. The photoacoustic reconstructions of the 250 micrometer carbon fiber rod in FIG. 11A resulted in echoes resembling comet trail artifacts, likely due to the proximity of the larger rod to the bottom of the petri dish. For the 250 micrometer carbon fiber rod in FIG. 11C, only the initial peak was measured as it corresponds to the full width half maximum of the target.

Example 3

7.2 Micrometer Carbon Fiber Thread with 2.5 Micrometer Steps

Figure 12A:
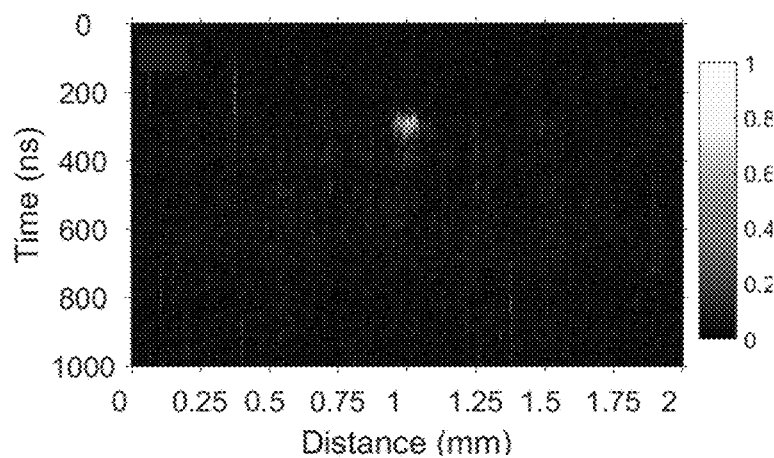
FIG. 12A is a photoacoustic image reconstruction of a 7.2 micrometer carbon fiber thread line target.
Figure 12B:
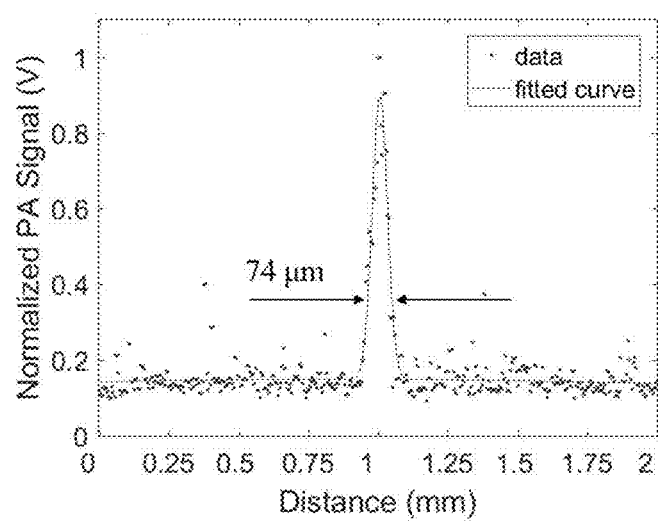
FIG. 12B is a graph of the maximum photoacoustic signals at different horizontal steps for a 7.2 micrometer line target.
Figure 12C:
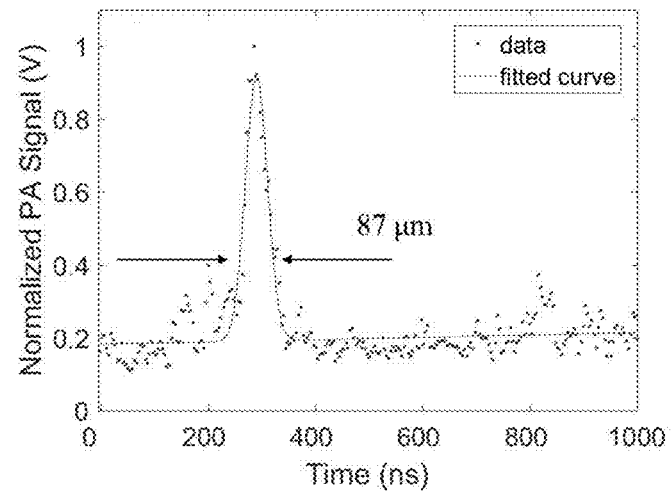
FIG. 12C is a graph of the maximum photoacoustic signals at different vertical steps for a 7.2 micrometer line target.

A 7.2 micrometer diameter carbon fiber thread was used as a line target in the example experimental setup depicted in FIG. 10A. The target was submerged in distilled water within a small petri dish container. The three-axis motorized stage was used to move the target horizontally in 2.5 micrometer steps. At each step, a laser was fired down the micropipette electrode and 1,000 nanoseconds of data from the resulting photoacoustic signal was acquired. A Hilbert Transform was applied to the data and the complex magnitude was subsequently calculated, normalized, and converted into a series of pixel values. This data is shown in FIG. 12A as a photoacoustic image reconstruction of the 7.2 micrometer line target. The maximum signal at each horizontal step for the 7.2 micrometer line target is shown in FIG. 12B. Using a Gaussian fit, the measured transverse full width half maximum of the 7.2 micrometer line target was 74 micrometers. This indicated that the resulting photoacoustic image was clearly indicative of the size of the target. A maximum signal generated along the vertical direction for the line target is displayed in FIG. 12C. Measuring the full width half maximum using a Gaussian fit and a speed of sound of 1,498 meters per second resulted in a value of 87 micrometers. The results of Examples 2 and 3 identify the ability of the micropipette electrode to horizontally locate targets of varying sizes, down to 7.2 micrometers.

Various embodiments and features are set forth in the following claims.

What is claimed is:

1. A photoacoustic targeting system, comprising a light source configured to emit pulsed light;
a micropipette electrode configured to deliver the pulsed light to a target cell, wherein the micropipette electrode includes a hollow tubular body and a tapered tip at a distal end of the hollow tubular body, wherein the tapered tip decreases in width as it extends from the hollow tubular body, and wherein the tapered tip includes an opening to a hollow interior of the hollow tubular body;
an acoustic transducer configured to receive photoacoustic signals generated due to optical absorption of light energy by the target cell; and
a controller configured to
determine a position of the micropipette electrode relative to the target cell based on the photoacoustic signals, wherein the target cell is a neuron, and
following movement of the micropipette electrode toward the target cell, capture electrophysiological intracellular recordings of the neuron through the micropipette electrode using patch clamp methods.

2. The photoacoustic targeting system of claim 1, wherein the hollow tubular body of the micropipette electrode includes a hollow tubular glass body covered with an aluminum coating.

3. The photoacoustic targeting system of claim 1, further comprising a lens configured to reduce a beam width of the pulsed light and including
a receiving face positioned relative to the light source to receive the pulsed light, and
an emitting face positioned relative to the micropipette electrode such that the pulsed light exiting the lens enters the micropipette electrode.

4. The photoacoustic targeting system of claim 3, wherein the lens is an achromatic doublet lens.

5. The photoacoustic targeting system of claim 3, wherein the lens is positioned such that the pulsed light enters the micropipette electrode on an edge of a sidewall of the hollow tubular body at a proximal end of the hollow tubular body.

6. The photoacoustic targeting system of claim 3, further comprising an optical fiber including a first end and a second end, wherein the first end of the optical fiber is positioned relative to the lens to receive the pulsed light, and wherein the second end of the optical fiber is positioned relative to the micropipette electrode such that the pulsed light exiting the second end of the optical fiber enters the micropipette electrode.

7. The photoacoustic targeting system of claim 6, wherein the second end of the optical fiber is positioned such that the pulsed light enters the micropipette electrode on a sidewall of the body.

8. The photoacoustic targeting system of claim 6, wherein the second end of the optical fiber is fused to the micropipette electrode.

9. The photoacoustic targeting system of claim 1, further comprising
a right angle prism positioned within the micropipette electrode and relative to the light source such that the pulsed light
enters the right angle prism at a first non-hypotenuse face of the right angle prism,
reflects off of a hypotenuse face of the right angle prism, and
exits the right angle prism at a second non-hypotenuse face of the right angle prism along a trajectory toward the tip of the micropipette electrode.

10. The photoacoustic targeting system of claim 9, wherein the right angle prism is positioned within the tip of the micropipette electrode.

11. The photoacoustic targeting system of claim 9, wherein the pulsed light enters the right angle prism along a first trajectory, wherein the pulsed light exits the right angle prism along a second trajectory, and wherein a reflection angle between the first trajectory and the second trajectory is substantially ninety degrees.

12. The photoacoustic targeting system of claim 9, further comprising a lens configured to reduce a beam width of the pulsed light and including
   a receiving face positioned relative to the light source to receive the pulsed light, and
   an emitting face positioned relative to the right angle prism such that the pulsed light exiting the lens enters the right angle prism at the first non-hypotenuse face of the right angle prism.

13. The photoacoustic targeting system of claim 12, wherein the lens is a grin lens.

14. The photoacoustic targeting system of claim 12, wherein the right angle prism is a first right angle prism, wherein the photoacoustic targeting system further comprising
   an optical fiber including
   a first end positioned relative to the light source to receive the pulsed light, and
   a second end positioned relative to the lens such that the pulsed light exiting the optical fiber enters the receiving face of the lens; and
   a second right angle prism positioned relative to the lens and the first right angle prism such that the pulsed light
       enters the second right angle prism at a first non-hypotenuse face of the second right angle prism,
       reflects off of a hypotenuse face of the second right angle prism, and
       exits the right angle prism at a second non-hypotenuse face of the second right angle prism toward the first non-hypotenuse face of the first right angle prism.

* * * * *